(12) United States Patent
Smith et al.

(10) Patent No.: US 6,376,194 B2
(45) Date of Patent: Apr. 23, 2002

(54) MIXED-BED SOLID PHASE AND ITS USE IN THE ISOLATION OF NUCLEIC ACIDS

(75) Inventors: Craig E. Smith, Oregon, WI (US); Diana L. Holmes, Crystal Lake, IL (US); Daniel J. Simpson, Middleton, WI (US); Jehoshua Katzenhendler, Jerusalem, IL (US); Rex M. Bitner, Cedarburg; Josephine C. Grosch, Mazomainie, both of WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/912,045

(22) Filed: Jul. 24, 2001

Related U.S. Application Data

(62) Division of application No. 09/312,139, filed on May 14, 1999, now Pat. No. 6,270,970.

(51) Int. Cl.$^7$ .......................... C12Q 1/68; C12P 19/34; G01N 31/00; C07H 19/00
(52) U.S. Cl. .......................... 435/6; 435/91; 435/803; 436/17; 536/27; 530/334; 935/1; 935/19; 935/20; 935/21; 935/77
(58) Field of Search .................. 435/6, 91, 803; 436/17; 536/27; 935/1, 19, 20, 21, 77; 530/334

(56) References Cited

U.S. PATENT DOCUMENTS

| | | | |
|---|---|---|---|
| 4,233,169 A | 11/1980 | Beall et al. ............... 252/62.59 |
| 4,297,337 A | 10/1981 | Mansfield et al. ............. 424/1 |
| 4,298,500 A | 11/1981 | Abbott .......................... 502/7 |
| 4,395,271 A | 7/1983 | Beall et al. ..................... 65/31 |
| 4,523,996 A | 6/1985 | Charles et al. ............. 210/504 |
| 4,672,040 A | 6/1987 | Josephson ................... 436/526 |
| 4,683,202 A | 7/1987 | Mullis ........................... 435/6 |
| 4,695,393 A | 9/1987 | Whitehead et al. ....... 252/62.54 |
| 4,699,717 A | 10/1987 | Riesner et al. .............. 210/635 |
| 4,767,670 A | 8/1988 | Cox et al. .................. 428/403 |
| 4,935,342 A | * 6/1990 | Seligson et al. ............... 435/6 |
| 5,057,426 A | 10/1991 | Henco et al. ................ 435/270 |
| 5,075,430 A | 12/1991 | Little ........................... 536/27 |
| 5,076,950 A | 12/1991 | Ullman et al. ......... 252/62.51 R |
| 5,155,018 A | 10/1992 | Gillespie et al. .............. 435/91 |
| 5,234,809 A | 8/1993 | Boom et al. ................ 435/91.2 |
| 5,316,680 A | 5/1994 | Frechet et al. .............. 210/635 |
| 5,346,994 A | 9/1994 | Chomczynski .............. 530/419 |
| 5,389,449 A | 2/1995 | Afeyan et al. ............... 428/523 |
| 5,395,498 A | 3/1995 | Gombinsky et al. ..... 204/182.8 |
| 5,523,231 A | 6/1996 | Reeve ......................... 435/270 |
| 5,582,988 A | 12/1996 | Backus et al. ................. 435/6 |
| 5,585,236 A | 12/1996 | Bonn et al. ..................... 435/5 |
| 5,610,274 A | 3/1997 | Wong ......................... 530/334 |
| 5,652,348 A | 7/1997 | Burton et al. ................. 536/20 |
| 5,654,141 A | 8/1997 | Mariani et al. ................. 435/6 |
| 5,658,548 A | 8/1997 | Padhye et al. ............... 423/335 |
| 5,660,984 A | 8/1997 | Davis et al. .................... 435/6 |
| 5,681,946 A | 10/1997 | Reeve ......................... 536/254 |
| 5,728,822 A | 3/1998 | Macfarlane ............... 536/25.41 |
| 5,734,020 A | 3/1998 | Wong ......................... 530/350 |
| 5,747,663 A | 5/1998 | Colpan et al. .............. 536/25.4 |
| 5,783,686 A | 7/1998 | Gonzalez ..................... 536/254 |
| 5,792,651 A | 8/1998 | Colpan et al. .............. 435/270 |
| 5,808,041 A | 9/1998 | Padhye et al. ............. 536/25.4 |
| 5,945,525 A | 8/1999 | Uematsu et al. ......... 536/25.42 |
| 5,990,301 A | 11/1999 | Colpan et al. .............. 536/25.4 |
| 6,027,945 A | 2/2000 | Smith et al. ................. 436/526 |

FOREIGN PATENT DOCUMENTS

| | | |
|---|---|---|
| CA | 2223821 | 6/1996 |
| DE | 43 07 262 A1 | 9/1994 |
| EP | 0757106 A2 | 2/1997 |
| GB | 2 074 892 A | 11/1981 |
| JP | 9327290 | 12/1997 |
| JP | 9327291 | 12/1997 |
| WO | WO 83/03363 | 10/1983 |
| WO | WO 95/06652 | 3/1995 |
| WO | WO 95/21179 | 8/1995 |
| WO | WO 96/16186 | 5/1996 |
| WO | WO 96/36706 | 11/1996 |
| WO | WO 97/29825 | 8/1997 |
| WO | WO 98/31461 | 7/1998 |
| WO | WO 98/31840 | 7/1998 |

OTHER PUBLICATIONS

Mariani et al., "Development of Novel, Rapid Processing Protocol for Polymerase Chain Reaction–Based Detection of Bacterial Infections in Synovial Fluids", *Molecular Biotechnology*, vol. 4. No. 3, 227–237 (1995).

Boom et al., "Rapid and Simple Method for Purification of Nucleic Acids", *J. Clin. Microbiol.*(1990) 28:495–503.

Marko et al., "A Procedure for the Large–Scale Isolation of Highly Purified Plasmid DNA Using Alkaline Extraction and Binding to Glass Powder", *Anal. Biochem.* (1982)121:382–387.

(List continued on next page.)

*Primary Examiner*—Jeffrey Fredman
*Assistant Examiner*—Arun Chakrabarti
(74) *Attorney, Agent, or Firm*—Michael Best & Friedrich LLP; Grady J. Frenchick

(57) ABSTRACT

Mixed-bed solid phases are provided, with methods for using such solid phases to isolate target nucleic acids, such as plasmid DNA, chromosomal DNA, RNA, or nucleic acids generated by enzymatic amplification from contaminants, including proteins, lipids, cellular debris, or other nucleic acids. The mixed-bed solid phases of this invention are mixtures of at least two different solid phases, each of which has a capacity to bind to the target nucleic acid under different solution conditions, and the capacity to release the nucleic acid under similar elution conditions. By exchanging solution conditions according to the methods of this invention, one can remove contaminants from the target nucleic acid bound to the mixed-bed solid phase, then elute the target nucleic acid in an elution buffer.

39 Claims, 3 Drawing Sheets

Promega, Technical Bulletin No. 202 Wizard® Plus Series 9600™ DNA Purification System, (Promega Corp.) (Sep. 1998).

Promega, Technical Bulletin No. 225 Wizard® Plus SV Minipreps DNA Purification System, (Promega Corp.) (Sep. 1999).

Promega, Technical Bulletin No. 259 Wizard® PureFection Plasmid DNA Purification System, (Promega Corp.) (Sep. 1999).

QuantiBlot, Human DNA Quantitation System, PE Applied Biosystems, Feb. 5, 1996, pp. 1–5 (http://www.pebio.com/fo/773503/773503.html).

Sambrook, Molecular Cloning a Laboratory Manual, 2nd ed. pp. 1.25–1.28 (1989).

Vogelstein et al., "Preparative and Analytical Purification of DNA from Agarose", *Proc. Natl. Acad. Sci.* (1979) vol. 76, No. 2:615–619.

Brown, et al., "Anion–Cation Separations on a Mixed Bed Alumina–Silica Column", J. Chromatog. (1989) vol. 466, No. 1 + index pp. 291–300.

Bitner, R., "Use of MagnaSil Paramagnetic Particles for Plasmid Purification, PCT Cleanup, and Purification of Dideoxy and Big Dye DNA Sequencing Reaction", *Proceedings of SPIE–Int. Soc. Opt. Eng.* (2000) vol. 3926, No. 3926, No. pp. 126–133.

Bischoff, Rainer and Larry W. McLaughlin. *Nucleic Acid Resolution By Mixed–Mode Chromatography. Journal of Chromatography* (1984) 296:329–337.

Bischoff, Rainer and Larry W. McLaughlin. *Chemically Synthesized Hydrophobic Anion–Exchange High–Performance Liquid Chromatography Supports Used for Oligonucleotide Resolution By Mixed Mode Chromatography. Journal of Chromatography.* (1983) 270:117–126.

Cotton, M. et al. 1994, *Gene Therapy* 1:239–246.

Crowother, Jonathan B. *High–Performance Liquid Chromatographic Separation of Oligonucleotides and Other Nucleic Acid Constituents on Multifunctional Stationary Phases. Journal of Chromatography* (1983) 282:619–628.

Edwardson P.A.D., et al. *Seperation and purification of oligonucleotides using a new bonded–phase packing material. Journal of Chromatography* (1991)545:79–89.

Floyd, Thomas R. et al., *Mixed–Mode Hydrophobic Ion Exchange for the Seperation of Oligonucleotides and DNA Fragments Using HPLC. Analytical Biochemistry* (1986) 154:570–577.

F. Ausubel et al., eds., *Current Protocols in Molecular Biology*, Wiley–Interscience, New York (1993).

Gjerde, Douglas T. *Ion Chromatography. Dr. Alfred Hothig Verlag Heidelberg* (1987) $2^{nd}$ Edition. New York.

Goldsborough, Mindy D. *High Purity Plasmid DNA from Anion Exchange Chromatography. Focus* (1998) vol. 20 No. 3.

Hirabayashi, Jun, *Applied slalom chromatography Improved DNA seperation by the use of columns developed for reversed–phase chromatography. Journal of Chromatography* (1996) 722:135–142.

Kirk–Othmer Encyclopedia of Chemical Technology, vol. 21, Mary Howe–Grant, ed., John Wiley & Sons, pub. 1997, pp. 1020–1023.

Little, Edward L. Mark S. Jeansonne, and Joe P. Foley. *Sequential Multimodal Elution for Pseudomultidimensional Liquid Chromatography on a Single Column. Anal. Chem* (1991) 63:33–44.

Maa, Yih–fen et al. *Rapid high–performance liquid chromatography of nucleic acids with polystyrene–based micropellicular anion exchangers. Journal of Chromatography* (1990)508:61–73.

Machrey–Nagel homepage on the Internet on Jun. 12, 1998, at http://www.machrey–nagel.com.

McLaughlin L. M., Chem Rev (1989) 89:309–319, at p. 309.

Molecular Cloning. ed. By Sambrook et al. (1989), pub. By Cold Spring Harbor Press, pp. 1.42–1.50.

Morrison. David C. 1987. *Ann Rev. Med.* 38:417–432.

Patent '680: Little E. L. et al., *Anal. Chem.* (1991) 63: 33.

Rassi Ziad El. and Csaba Horvath. *Tandem Columns and Mixed–Bed Columns in High–Performance Liquid Chromatography of Proteins. Journal of Chromatography.* (1986) 359:255–264.

W. Jost, et al. *J. Chromatog.* 185 (1979) 403–412.

Waterborg, Jakob H. and Anthony J. Robertson. *Efficient large–scale purification of restriction fragments by solute–displacement ion–exchange HPLC. Nucleic Acids Research* (1993) vol. 21. No. 12:2913–2915.

Weber, M. et al. 1995 , *Biotechniques* 19(6):930–939.

Wheatley J. B., J. *Chromatogr.* (1992) 603–273.

ABBASZADEGAN et al., "Detechon of Enteroviruses in Groundwater with the PCR", Applied & Enviromental Microbiology, vol. 59(5), pp. 1318–1324., May 1993.*

* cited by examiner

PLASMID DNA BAND EXCISION

TOTAL RNA AND DNA ISOLATED FROM MOUSE BLOOD

TOTAL RNA ISOLATED FROM MOUSE LIVER under another set of solution conditions. More particularly, this invention relates to mixed-bed solid phases comprising at least two different solid phases, wherein each solid phase in the mixture binds to and releases a target nucleic acid under different conditions.

MIXED-BED SOLID PHASE AND ITS USE IN THE ISOLATION OF NUCLEIC ACIDS

CROSS-REFERENCE TO RELATED APPLICATIONS

This application is a divisional of U.S. application Ser. No. 09/312,139, filed May 14, 1999, now U.S. Pat. No. 6,270,970.

STATEMENT REGARDING FEDERALLY SPONSORED RESEARCH OR DEVELOPMENT

Not Applicable

TECHNICAL FIELD

This invention relates generally to materials and methods for isolating nucleic acids, such as plasmid DNA, chromosomal DNA, total RNA, mRNA, viral DNA, viral RNA, or RNA/DNA hybrids from contaminants, such as proteins, lipids, cellular debris, or other nucleic acids. This invention relates, particularly, to solid phases, including magnetic or non-magnetic matrices and chromatographic stationary phases, which bind to a target nucleic acid under one set of solution conditions and release the target nucleic acid under another set of solution conditions. More particularly, this invention relates to mixed-bed solid phases comprising at least two different solid phases, wherein each solid phase in the mixture binds to and releases a target nucleic acid under different conditions.

BACKGROUND

Many molecular biological techniques such as reverse transcription, cloning, restriction analysis, amplification and sequencing require that nucleic acids used in the techniques be substantially free of contaminants capable of interfering with such processing or analysis procedures. Such contaminants generally include substances that block or inhibit chemical reactions, (e.g. substances that hybridize to nucleic acids, or substances that block or inhibit enzymatically catalyzed reactions, and other types of reactions used in molecular biological techniques), substances that catalyze the degradation or depolymerization of a nucleic acid or other biological material of interest, or substances which block or mask detection of the nucleic acid of interest. Substances of this last type can block or mask by providing a "background" indicative of the presence in a sample of a quantity of a nucleic acid of interest, (also referred to herein as a "target nucleic acid") when the nucleic acid of interest is not, in fact, present in the sample. Contaminants also include macromolecular substances from the in vivo or in vitro medium from which a target nucleic acid is isolated, macromolecular substances such as enzymes, other types of proteins, polysaccharides, or polynucleotides, as well as lower molecular weight substances, such as lipids, low molecular weight enzyme inhibitors, oligonucleotides, or non-target nucleic acids. Contaminants can also be introduced into a target biological material from chemicals or other materials used to isolate the material from other substances. Common contaminants of this last type include trace metals, dyes, and organic solvents.

Obtaining target nucleic acid, which is sufficiently free of contaminants for molecular biological applications, is complicated by the complex systems in which the target nucleic acid is typically found. Such systems (e.g., cells from tissues, cells from body fluids such as blood, lymph, milk, urine, feces, semen, or the like, cells in culture, agarose or polyacrylamide gels, or solutions in which target nucleic acid amplification has been carried out) typically include significant quantities of contaminants from which the target nucleic acid of interest must be isolated before being used in a molecular biological procedure.

Endotoxins are particularly problematic contaminants in preparations of nucleic acids isolated from gram-negative bacilli. Generally speaking, an endotoxin is a lipopolysaccharide material found in the cell wall of most such bacilli, including *Escherichia Coli* ("*E. coli*"). During lysis of bacterial cells, such as is done to release plasmid DNA from *E. coli* transformants, endotoxins are released into the lysate produced thereby. Endotoxin contamination in a nucleic acid sample can adversely limit the utility of the sample, particularly in applications, which are sensitive to such contamination. For example, the transfection efficiency of several different cultured eukaryotic cell lines, including HeLa, Huh7, COS7, and LMH, have been shown to be sharply reduced in the presence of endotoxins. Weber, M. et al. 1995, *BioTechniques* 19(6):930–939. Endotoxins have also been found to be toxic to primary human cells, such as primary human skin fibroblasts and primary human melanoma cells, in the presence of entry-competent adenovirus particles. Cotten, M. et al. 1994, *Gene Therapy* 1:239–246. Endotoxins have also been shown to produce striking pathophysiological reactions when introduced into animals, including high fever, vasodilation, diarrhea and, in extreme cases, fatal shock. Morrison, David C. 1987, *Ann. Rev. Med.* 38:417–32.

Endotoxins are not readily separated from nucleic acids, particularly from plasmid DNA. Endotoxins tend to form micelles, which have a similar density, size, and charge distribution to plasmid DNA on the outer surface of the endotoxin micelles. As a result, endotoxins co-purify with nucleic acids, particularly with plasmid DNA, in most nucleic acid isolation procedures used today. For example, endotoxins appear in the same band as the DNA-ethidium bromide complex in the cesium chloride gradients used to separate plasmid DNA from other materials in a bacterial lysate. Endotoxins also co-migrate and co-elute with plasmid DNA from size exclusion and from anion exchange resins.

Conventional protocols for isolating DNA or RNA from various types of cells, including bacteria, begin with the cell disruption steps. See, e.g. Chapter 2 (DNA) and Chapter 4 (RNA) of F. Ausubel et al., eds., *Current Protocols in Molecular Biology*, Wiley-Interscience, New York (1993). Conventional DNA isolation protocols generally entail suspending the cells in a solution and using enzymes and/or chemicals, gently to lyse the cells, thereby releasing the DNA contained within the cells into the resulting lysate solution. For RNA isolation, conventional lysis and solubilization procedures include measures for inhibition of ribonucleases and contaminants, including DNA, to be separated from the RNA.

Many conventional procedures for isolating target nucleic acids from various mixtures of the target nucleic acids and contaminants, including mixtures produced from cells as described above, entail the use of hazardous chemicals such as phenol, chloroform, and ethidium bromide. For example, phenol or an organic solvent mixture containing phenol and chloroform are used in many such conventional procedures to extract contaminants from mixtures of target nucleic acids and various contaminants. Alternatively, cesium chloride-ethidium bromide gradients are used in place of or in addition to phenol or phenol-chloroform extraction. Closed circular DNA, such as plasmid DNA, intercalates with ethidium bromide and forms a band in a cesium chloride gradient formed after several hours of ultracentrifugation. The DNA/ethidium bromide band is extracted therefrom and the plasmid DNA isolated from the ethidium bromide using butanol or other conventional means. See, e.g., *Molecular Cloning*, ed. by Sambrook et al. (1989), pub. by Cold Spring Harbor Press, pp. 1.42–1.50. The phenol/chloroform extraction step, or cesium chloride banding and ethidium bromide extraction step is generally followed by precipitation of the nucleic acid material remaining in the extracted aqueous phase by adding ethanol to that aqueous phase. The precipitate is typically removed from the solution by centrifugation, and the resulting pellet of precipitate is allowed to dry before being resuspended in water or a buffer solution for further processing or analysis.

Such conventional nucleic acid isolation procedures have significant drawbacks. Among these drawbacks are the large amount of time required for multiple processing and extraction steps, and the dangers of using phenol and/or chloroform. Phenol causes severe burns on contact. Chloroform is highly volatile, toxic, and carcinogenic. Those characteristics require that phenol be handled and phenol/chloroform extractions be carried out in a fume hood. Another undesirable characteristic of phenol/chloroform extractions is that the oxidation products of phenol can damage nucleic acids. Only freshly redistilled phenol can be used effectively, and nucleic acids cannot be left in the presence of phenol. Generally also, multi-step procedures are required to isolate RNA after phenol/chloroform extraction. Ethanol (or isopropanol) precipitation must be employed to precipitate the DNA from a phenol/chloroform-extracted aqueous solution of DNA and remove residual phenol and chloroform from the DNA. Further, ethanol (or isopropanol) precipitation is required to remove some nucleoside triphosphate and short (i.e., less than about 30 bases or base pairs) single or double-stranded oligonucleotide contaminants from the DNA. Moreover, under the best circumstances such methods produce relatively low. yields of isolated nucleic acid material, and the isolated nucleic acid material is contaminated with impurities.

Cesium chloride gradients take time to form, requiring at least four hours of spin time in even the fastest, most modem centrifuges. Ethidium bromide, required for banding of plasmid or chromosomal DNA such gradients, is a mutagen. Also, when cesium chloride banding is used to isolate plasmid DNA from bacterial lysates without any preceding or succeeding protein extraction step, such as a phenol/chloroform extraction, the plasmid DNA isolated therewith has been found to be highly contaminated with endotoxins. See, e.g. Cotten, et al., *Gene Therapy* (1994) 1:239–146, at 240 [Table 1].

Several simpler, faster, and safer methods have been developed which utilize solid phases such as chromatographic resins or silica-based material to isolate nucleic acids from cell lysates or other mixtures of nucleic acids and contaminants. However, each such isolation system developed so far has its own unique drawbacks. Specifically, most such solid phase extraction systems either fail to eliminate undesirable contaminants, such as endotoxins, or they introduce undesirable contaminants not present in an initial nucleic acid mixture, such as proteases or corrosive salts. Each such contaminant must be removed using additional extraction steps before the nucleic acid isolated therewith can be used in applications sensitive to such contaminants.

One of the first solid phases developed for use in isolating nucleic acids was a specialized resin of porous silica gel particles designed for use in high performance liquid chromatography (HPLC). The surface of the porous silica gel particles was functionalized with anion-exchangers, which could exchange with plasmid DNA under certain salt and pH conditions. See, e.g. U.S. Pat. Nos. 4,699,717, and 5,057, 426. Machrey-Nagel Co. (Düren, Germany), one of the first companies to provide HPLC columns packed with such anion-exchange silica gel particles. Machrey-Nagel continues to sell such columns today. See, e.g. formation about NUCLEOGEN® 4000-7DEAE in product information downloaded from the Machrey-Nagel homepage on the Internet on Jun. 12, 1998, at http://www.machrey-nagel.com. Each such column was designed so that plasmid DNA bound thereto is eluted in an aqueous solution containing a high concentration of a highly corrosive salt (e.g. plasmid DNA is eluted from the NUCLEOGEN® 4000-7DEAE column in 6 M urea). Each such column had to be washed thoroughly between each isolation procedure to remove the corrosive salt and contaminants bound to the column with the DNA from the system. The nucleic acid solution eluted therefrom also had to be processed further to remove the corrosive salt therefrom before it could be used in standard molecular biology techniques, such as cloning, transformation, digestion with restrictive enzymes, or amplification.

Various silica-based solid phase separation systems have been developed since the early HPLC systems described above. Modem silica-based systems utilize controlled pore glass, filters embedded with silica particles, silica gel particles, resins comprising silica in the form of diatomaceous earth, glass fibers or mixtures of the above. Each modem silica-based solid phase separation system is configured to reversibly bind nucleic acid materials when placed in contact with a medium containing such materials in the presence of chaotropic agents. Such solid phases are designed to remain bound to the nucleic acid material while the solid phase is exposed to an external force such as centrifugation or vacuum filtration to separate the matrix and nucleic acid material bound thereto from the remaining media components. The nucleic acid material is then eluted from the solid phase by exposing the solid phase to an elution solution, such as water or an elution buffer. Numerous commercial sources offer silica-based resins designed for use in centrifugation and/or filtration isolation systems. See, e.g. Wizard™ DNA purification systems products from Promega Corporation (Madison, Wis., U.S.A.); or the QiaPrep™ DNA isolation systems from Qiagen Corp. (Santa Clarita, Calif., U.S.A.)

Magnetically responsive particles, formerly used to isolate and purify polypeptide molecules such as proteins or antibodies, have also been developed for use as solid phases in isolating nucleic acids. Several different types of magnetically responsive particles designed for isolation of such materials are described in the literature, and many of those types of particles are available from commercial sources. Such particles generally fall into either of two categories, those designed to reversibly bind nucleic acid materials directly, and those designed to reversibly bind nucleic acid materials through an intermediary. For an example of particles of the first type, see silica based porous particles designed to reversibly bind directly to DNA, such as MagneSil™ particles to be made commercially available from Promega Corporation, or BioMag® magnetic particles available from PerSeptive Biosystems. For examples of particles and systems of the second type designed to reversibly bind one particular type of nucleic acid (mRNA), see the PolyATract® Series 9600™ mRNA Isolation System from Promega Corporation; or the ProActive™ line of streptavidin coated microsphere particles from Bangs Laboratories (Cannel, Ind., U.S.A.). Both of these latter two systems employ magnetically responsive particles with avidin subunits covalently attached thereto, and streptavidin with an oligo dT moiety covalently attached thereto. The streptavidin-oligo dT molecules act as intermediaries, hybridizing to the poly A tail of mRNA molecules when placed into contact therewith, then binding to the particles through a releasable streptavidin-avidin bond.

The indirect binding magnetic separation systems for nucleic acid isolation or separation all require at least three components, i.e. magnetic particles, an intermediary, and a medium containing the nucleic acid material of interest. The intermediary/nucleic acid hybridization reaction and intermediary/particle binding reaction often require different solution and/or temperature reaction conditions from one another. Each additional component or solution used in the nucleic acid isolation procedure adds to the risk of contamination of the isolated end product by nucleases, metals, and other deleterious substances.

Various types of magnetically responsive silica based particles have been developed for use as solid phases in direct or indirect nucleic acid binding isolation methods. One such particle type is a magnetically responsive glass bead, preferably of a controlled pore size. See, e.g. Magnetic Porous Glass (MPG) particles from CPG, Inc. (Lincoln Park, N.J., U.S.A.); or porous magnetic glass particles described in U.S. Pat. Nos. 4,395,271; 4,233,169; or 4,297,337. Nucleic acid material tendsto bind very tightly to glass, however, that it can be difficult to remove once bound thereto. Therefore, elution efficiencies from magnetic glass particles tend to be low compared to elution efficiencies from particles containing lower amounts of a nucleic acid binding material such as silica.

Another type of magnetically responsive particle designed for use as a solid phase in direct binding and isolation of nucleic acids, particularly DNA, is a particle comprised of agarose embedded with smaller ferromagnetic particles and coated with glass. See, e.g. U.S. Pat. No. 5,395,498. A third type of magnetically responsive particle designed for direct binding and isolation of nucleic acids is produced by incorporating magnetic materials into the matrix of polymeric silicon dioxide compounds. See, e.g. German Patent No. DE 43 07 262 A1. The latter two types of magnetic particles, the agarose particle and the polymeric silicon dioxide matrix, tend to leach iron into a medium under the conditions required to bind nucleic acid materials directly to each such magnetic particle. It is also difficult to produce such particles with a sufficiently uniform and concentrated magnetic capacity to ensure rapid and efficient isolation of nucleic acid materials bound thereto.

Silica-based solid phase nucleic acid isolation systems, whether magnetic or non-magnetic based or configured for direct or indirect binding, are quick and easy to use and do not require the use of corrosive or hazardous chemicals. However, such systems are ineffective at isolating nucleic acids from contaminants, such as endotoxins, which tend to bind to and elute from such solid supports under the same conditions as nucleic acids. See, e.g. Cotten, Matt et al. *Gene Therapy* (1994) 1:239–246.

Some nucleic acid isolation systems have been developed in which a nucleic acid solution containing proteins is pretreated with proteases to digest at least some of the proteins contained therein prior to isolation of the nucleic acid using a silica-based solid support of the type described above. See, e.g., QiaAmp™ Blood Kit provided by QIAGEN Inc. (Santa Clarita, Calif.), which utilizes protease; and Wizard® Plus SV Minipreps DNA Purification System provided by Promega Corp. (Madison, Wis.), which utilizes an alkaline protease. However, such pre-treatment systems require the introduction of one contaminant into a mixture to digest another contaminant. Carry-over proteases can limit the utility of nucleic acids isolated using such modified silica-based systems at least as much as nucleic acid samples contaminated with the proteins the proteases are introduced to digest. Specifically, given the proper solution conditions, proteases in a nucleic acid solution will digest any proteins introduced into the solution, including enzymes introduced therein to modify, cut, or transcribe the nucleic acid contained therein for downstream processing or analysis. Protease addition, incubation and removal steps also drive up the cost of nucleic acid isolation, costing time and money compared to isolation systems with no such additional steps.

In all the solid phase systems described above, each solid phase used therein has a substantially uniform surface composition designed to bind to a nucleic acid of interest, in the form of a silica or silica gel surface, or in the form of a silica gel or polymer surface modified with chemical groups exhibiting anion exchanger activities. Bimodal and multi-modal systems have also been developed, in which multiple columns each of which contains a solid phase modified with a different chemical group from the other columns in the system (e.g., Wheatley J. B., *J. Chromatogr.* (1992) 603: 273), or in which a single column is used with a single solid phase with at least two different chemical groups (e.g., patent '680; Little, E. L. et al., *Anal. Chem.* (1991) 63: 33). Each of the chemical groups on the surface of the solid supports in the single column or multicolumn multimodal systems is configured to bind to different materials in whatever substrate is introduced into the system. Only a few such bimodal or multimodal column chromatography systems have been developed specifically for nucleic acid isolation (see, e.g. U.S. Pat. No. 5,316,680). Surface group combinations used in such solid phase systems include reverse phase, ion exchange, size exclusion, normal phase, hydrophobic interaction, hydrophilic interaction, and affinity chromatography. Such systems are designed such that only one of the surface groups binds a target species, such as a nucleic acid, while the other surface group(s) bind to and remove one or more non-target species in a mixture.

The bimodal and multimodal systems are far from simple, efficient alternatives to conventional organic or resin methods of nucleic acid isolation described above. Multi-column systems are inherently complex to run, as each column has requires a unique set of mobile phase conditions to bind and/or release the desired target or non-target species bound to the stationary solid phase of the system. Non-target species tend to block adjacent functional groups configured to bind to the target species, thus adversely affecting overall yield. Also, all the bimodal or multimodal systems are only designed to separate a target species from other species for which functional groups have affinity.

Materials and methods are needed which can quickly, safely, and efficiently isolate target nucleic acids which are sufficiently free of contaminants, particularly endotoxins, to be used in molecular biology procedures. The present invention addresses the need for materials and methods which provide a rapid and efficient means for isolating target nucleic acids from any mixture of target nucleic acids and contaminants, including lysates of gram-negative bacteria, thereby providing purified nucleic acids which can be used in a variety of biological applications, including transfection of cultured cells and in vivo administration of nucleic acids to organisms.

BRIEF SUMMARY OF THE INVENTION

Briefly, in one aspect, the present invention is a mixed-bed solid phase designed for use in isolating a target nucleic acid from a mixture comprising the target nucleic acid and at least one contaminant. In a preferred practice, multiple contaminants are included in the mixture. The mixed-bed solid phase comprises at least two different solid phases, each of which has a capacity to bind and to release the target nucleic acid in the presence of different solution conditions.

The mixed-bed solid phase of the present invention preferably comprises a first solid phase and a second solid phase, wherein:

the first solid phase has a capacity to bind to the target nucleic acid when combined with the mixture in the presence of a first solution, and a capacity to release the target nucleic acid bound thereto in the presence of a second solution;

the second solid phase has a capacity to bind to the target nucleic acid when combined with the mixture in the presence of the second solution, and a capacity to release the target nucleic acid bound thereto in the presence of the first solution; and the first solid phase and the second solid phase each have a capacity to release the target nucleic acid bound thereto in the presence of an elution buffer.

In another aspect, the present invention is a mixed-bed solid phase for isolating a target nucleic acid from a mixture comprising the target nucleic acid and at least one contaminant, the mixed-bed solid phase comprising first silica magnetic particles and second silica magnetic particles, wherein:

(a) the first silica magnetic particles have a capacity to bind to the target nucleic acid when combined with the mixture in the presence of a first solution, and a capacity to release the target nucleic acid bound thereto in the presence of a second solution;

(b) the second silica magnetic particles have a capacity to bind to the target nucleic acid when combined with the mixture in the presence of the second solution, and a capacity to release the target nucleic acid bound thereto in the presence of the first solution; and (c) the first silica magnetic particles and the second silica magnetic particles all have the capacity to release the target nucleic acid bound thereto in the presence of an elution buffer.

In this aspect of the present invention, the first silica magnetic particles and second silica magnetic particles are either silica magnetic particles each comprising at least one ion exchange residue covalently attached thereto, or silica magnetic particles comprising a siliceous oxide coating and no anion exchange residue, respectively. The ion exchange residue is either an anion exchange residue, or an ion exchange residue which has a positive charge in the presence of the first or second solution, such that it can exchange with the target nucleic acid within that solution.

In another aspect, the present invention is silica magnetic particles, comprising: a plurality of first silica magnetic particles, each of which comprises a first silica magnetic particle covalently attached to a diethylamino (DEA) anion exchange residue. Such DEA ion exchange silica magnetic particles are particularly suitable for use as one of the solid phases in the mixed-bed solid phase of the present invention described above, and in the methods of isolating a target nucleic acid of the present invention described below.

The present invention is, also, a method of isolating a target nucleic acid from a mixture comprising the target nucleic acid and at least one contaminant, using a mixed-bed solid phase comprising a first solid phase and a second solid phase. This method comprises the steps of:

(a) providing the mixed-bed solid phase;

(b) combining the mixture with the mixed-bed solid phase in the presence of a first solution and permitting the target nucleic acid to bind to the first solid phase;

(c) separating the mixed-bed solid phase from the first solution;

(d) combining the mixed-bed solid phase with a second solution, and permitting the target nucleic acid to release from the first solid phase and bind to the second solid phase;

(e) separating the mixed-bed solid phase from the second solution; and (f) combining the mixed-bed solid phase with the elution buffer, and permitting the target nucleic acid to release from the mixed-bed solid phase into the elution buffer.

This embodiment of the present invention preferably further comprises additional steps, wherein the mixed-bed solid phase is recombined and separated from the first solution and the second solution prior to being combined with the elution buffer in step (f).

The methods and materials of the present invention can be used to isolate target nucleic acids including, but not limited to plasmid DNA, total RNA, amplified nucleic acids, and genomic DNA from a variety of contaminants, including but not limited to agarose and components of a bacteria, animal tissue, and blood cells other than the target nucleic acid.

The mixed-bed solid phase and method of this invention enable one to isolate a variety of different types of target nucleic acids quickly and efficiently from a variety of difference substances, without the need to use hazardous chemicals (e.g. phenol, chloroform, ethidium bromide, or cesium chloride). Without intent to limit the scope of the present inventions, it is proposed herein that the first solid phase and second solid phase work more efficiently in the mixed-bed configuration of the present invention than either phase would if used to isolate a target nucleic acid alone, in tandem, or as separate functional groups of the same solid phase, for the following reasons.

A mixed-bed configuration enables one to transfer the target nucleic acid back and forth from the first solid phase to the second solid phase, thereby, further isolating the target nucleic acid from contaminants associated therewith, with each transfer step. When only one of the solid phases is used to isolate the target nucleic acid, considerably fewer of the contaminants are removed.

When used in tandem, the target nucleic acid is only bound to and released from each solid phase once, leaving at least one contaminants i.e. the target nucleic acid mixture. When two different functional groups having different affinities for the target nucleic acid are provided on the same solid phase, the target nucleic acid is not as efficiently bound and released therefrom as it is transferred from one solid phase to another using the mixed-bed solid phase in the method of the present invention. The mixed-bed solid phase produces surprising and unexpected results compared to known solid phase systems or other chromatographic separation techniques.

Target nucleic acids isolated using the mixed-bed solid phase or methods of the present invention are sufficiently free of contaminants to be suitable for use in additional processing, analysis, or even administration to mammals. Applications of the present mixed-bed solid phase to isolate nucleic acids from a variety of different media will become apparent from the detailed description of the invention below. Those skilled in the art of this invention will appreciate that the detailed description of the invention is meant to be exemplary only and should not be viewed as limiting the scope of the invention.

BRIEF DESCRIPTION OF THE DRAWING(S)

DETAILED DESCRIPTION OF THE INVENTION

Figure 1:
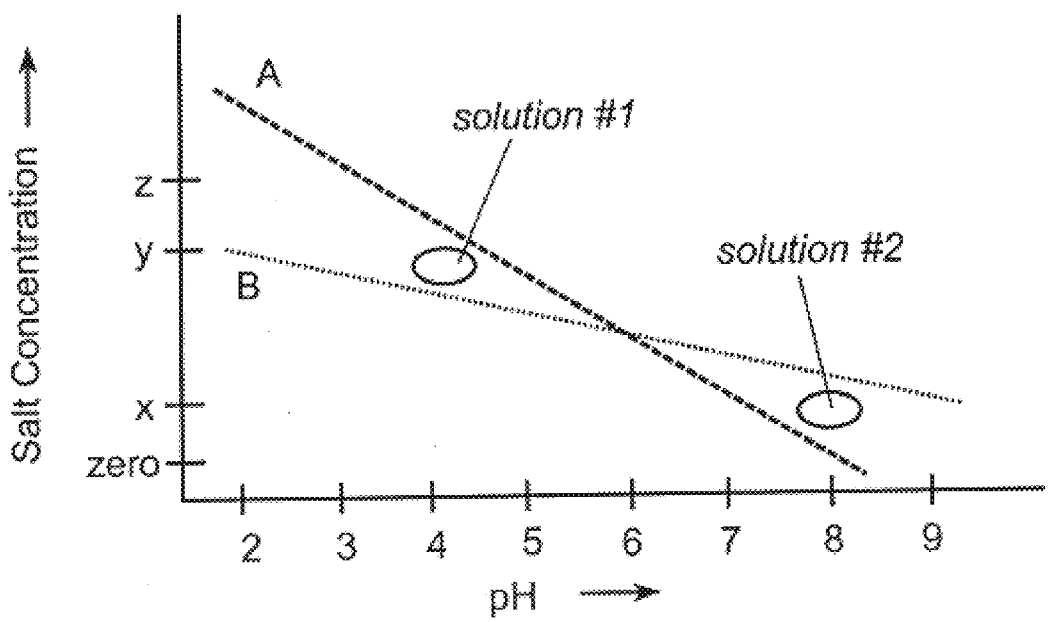
FIG. 1 is a theoretical plot of the binding activity of two different anion-exchange solid phases, one (triangles) having a pKa which is significantly lower than the pKa of the second (circles).

The term "solid phase", is used herein in a standard chromatographic sense, to refer to an insoluble, usually rigid, matrix or stationary phase which interacts with a solute, in this case a target nucleic acid, in a solute mixture. The term solid phase, as used herein, specifically includes stationary phases in liquid chromatography(LC), high pressure liquid chromatography (HPLC), particulate matrices embedded into or bound to filters, and magnetic or non-magnetic porous or non-porous matrix particles which interact with solutes when added directly to a solute mixture.

The terms "first solid phase" and "second solid phase" as used herein, refer to separate and distinct solid phase media (e.g. separate resins, matrix, particle, or filter media) each of which has a different affinity for the target nucleic acid solute in the solute mixture.

The term "mixed-bed solid phase", as used herein, refers to at least two different solid phases in a single container or column (e.g., a first solid phase and a second solid phase), wherein each solid phase in the mixed-bed has a different affinity for the solute. The mixed-bed solid phase can be in any one of a number of different forms or mixtures of forms, including a mixture of at least two different types of chromatography particles (such as a mixture of reversed-phase and ion exchange particles, or a mixture of ion exchange particles with different affinities for a particular target nucleic acid), a mixture of at least two different types of silica magnetic particles (e.g., a mixture of silica magnetic particles wherein the surfaced of one species of particle in the mixture is either silica gel or glass with no functional group attached thereto or silica gel or glass with a siliceous oxide coating, while another species of particle in the mixture has an ion exchange group covalently attached thereto), or a combination of at least two different filters with a different type of particle or functional group bound thereto or embedded therein. Regardless of the form in which each solid phase in the mixed-bed solid phase is presented, the affinity of each solid phase for a given solute depends upon the composition of the solid phase, including the composition of the surface of each solid phase particle. Affinity for target nucleic acids in the mixed-bed solid phase of the present invention can be through any one of a number of means typically used to bind a solute to a solid phase including, but not limited to, ionic interactions (e.g., anion-exchange chromatography) and hydrophobic interactions (e.g., reversed-phase chromatography).

The term "silica gel" as used herein refers to chromatography grade silica gel, a substance which is commercially available from a number of different sources. Silica gel is most commonly prepared by acidifying a solution containing silicate, e.g. sodium silicate, to a pH of less than 10 or 11 and then allowing the acidified solution to gel. See, e.g. silica preparation discussion in *Kurt-Othmer Encyclopedia of Chemical Technology*, Vol. 21, Mary Howe-Grant, ed., John Wiley & Sons, pub. 1997,pp. 1020–1023.

The term "glass particles" as used herein means particles of crystalline silicas (e.g., α-quartz, vitreous silica), even though crystalline silicas are not formally "glasses" because they are not amorphous, or particles of glass made primarily of silica.

As used herein, the term "silica magnetic particles" refers to silica matrices which are further comprised of materials which have no magnetic field but which form a magnetic dipole when exposed to a magnetic field, i.e., materials capable of being magnetized in the presence of a magnetic field but which are not themselves magnetic in the absence of such a field. The term "magnetic" as used in this context includes materials which are paramagneticor super paramagnetic materials. The term "magnetic", as used herein, also encompasses temporarily magnetic materials, such as ferromagnetic or ferrimagnetic materials. Except where indicated otherwise below, the silica magnetic particles used in this invention preferably comprise a superparamagnetic core coated with siliceous oxide, having a hydrous siliceous oxide adsorptive surface (i.e. a surface characterized by the presence of silanol groups).

The term "chaotropic agent" as used herein refers to salts of particular ions which, when present in a sufficiently high concentration in an aqueous solution, cause proteins present therein to unfold and nucleic acids to lose secondary structure. It is thought that chaotropic ions have these effects because they disrupt hydrogen-bonding networks that exist in liquid water and thereby make denatured proteins and nucleic acids thermodynamically more stable than their correctly folded or structured counterparts. Chaotropic ions include guanidinium, iodide, perchlorate, and trichloroacetate. Chaotropic agents include guanidine hydrochloride, guanidine thiocyanate (which is sometimes referred to as guanidine isothiocyanate), sodium iodide, sodium perchlorate, and sodium trichloroacetate.

The first solid phase and second solid phase components of the mixed-bed solid phase of the present invention each have a capacity to bind to and release the target nucleic acid under different solution conditions. The first solid phase has the capacity to bind to the target nucleic acid in the presence of a first solution and to release the target nucleic acid in the presence of a second solution, while the second solid phase has the capacity to bind the target nucleic acid in the presence of the second solution and to release the target nucleic acid in the presence of the first solution. Thus, when the mixed-bed solid phase is combined with a mixture of the target nucleic acid and at least one contaminant in the presence of the first solution, the target nucleic acid binds to the first solid phase. When the mixed-bed solid phase is then separated from the first solution and combined with the second solution, the target nucleic acid is released from the first solid phase and binds to the second solid phase. The mixed-bed solid phase is then separated from the second solution and combined with an elution buffer, wherein the target nucleic acid is released into the elution buffer. The mixed-bed solid phase is preferably combined with the first solution and separated therefrom, and/or combined with the second solution and separated therefrom at least one additional time before being combined with the elution buffer.

The first solid phase and the second solid phase can be made of any common support material, including soft gel supports such as agarose, polyacrylamide, or cellulose, or hard support material such as polystyrene, latex, methacrylate, or silica. When the solid phase support material is silica, it is preferably in the form of silica gel, siliceous oxide, solid silica such as glass or diatomaceous earth, or a mixture of two or more of the above. At least one of the solid phases in the mixed-bed solid phase preferably comprises a silica gel particle. Silica gel particles are stable at much higher pressures than solid phases made from soft gel support material, making the silica gel solid phases suitable for HPLC, as well as for LC and batch separation applications. Silica materials, such as silica gel particles, can bind target nucleic acids in the presence of chaotropic agents. Silica materials can also bind at least one contaminant, such as endotoxins, in the absence of such agents.

The mixed-bed solid phase mix used in the present invention is preferably in a form which can be separated from a solute mixture comprising the target nucleic acid and at least one contaminant after the solute mixture is combined therewith, by application of an external force. A skilled artisan would appreciate that the type of external force suitable for use in separating the mixed-bed solid phase mix from the solute mix depends upon the form in which the mixed-bed solid phase mix is presented to the solute mix, and upon the physical properties of the mixed-bed solid phase itself. For example, gravity can be used to separate the mixed-bed solid phase from the solute mix when the mixed-bed solid phase is a mixed-bed resin loaded on an LC column, when the mixed-bed solid phase is a mixed-bed resin or mixture of controlled pore particles (e.g. silica based particles) which are added batch-wise to a solute mixture and then separated therefrom by decantation or filtration, or when the mixed-bed solid phase is embedded into or attached to a filter through which the solute mixture passes. The external force is high pressure liquid when the mixed-bed solid phase forms the stationary phase of a high pressure liquid chromatography column (HPLC). Other forms of external force suitable for use in the method of this invention include vacuum filtration (e.g. when the mixed-bed solid phase is particles of controlled pore glass, mixed-bed solid phase particles such as a mix of other silica-based particles, or embedded into or attached to a filter), centrifugation (e.g. when the mixed-bed solid phase is particulate), or magnetic (e.g. when the mixed-bed solid phase comprises magnetic or paramagnetic particles).

Silica materials, particularly silica gel, can be configured for use in the mixed-bed solid phase of the present invention wherein any one or more of the removal means cited above is used. Silica based solid phases particularly preferred for use as the first or second solid phases in the mixed-bed solid phase of the present invention include solid phases described in PCT Publication Number WO 95/06652, U.S. Pat. No. 6,658,548, PCT Publication Number WO 98/31840 and solid phases sold by Promega Corporation for use in plasmid DNA isolation, i.e. Wizards® Minipreps DNA Purification Resin, all of which are incorporated herein by reference.

When the first or second solid phase is a silica gel particle which is magnetic, it is preferably a silica magnetic particle, more preferably a siliceous oxide coated (SOCM) silica magnetic particle as disclosed in PCT Publication Number PCT/US98/01149, published as WO 98/31461 on Jul. 23, 1998. A silica magnetic particle can be separated from a solution using any of the external means described above for use with other silica matrices. But, the external means used to separate a silica magnetic particle from a solution is preferably magnetic force. The first solid phase and second solid phase are preferably both silica magnetic particles.

When either the first or second silica matrix is a silica magnetic particle, the size of the particle is preferably selected as follows. Smaller silica magnetic particles provide more surface area (on a per weight unit basis) for adsorption, but smaller particles are limited in the amount of magnetic material which can be incorporated into such particles compared to larger particles. The median particle size of the silica magnetic particles used in a particularly preferred embodiment of the present invention is about 1 to 15 $\mu$m, more preferably about 3 to 10 $\mu$m, and most preferably about 4 to 7 $\mu$m. The particle size distribution may also be varied. However, a relatively narrow monodal particle size distribution is preferred. The monodal particle size distribution is preferably such that about 80% by weight of the particles are within a 10 $\mu$m range about the median particle size, more preferably within an 8 $\mu$m range, and most preferably within a 6 $\mu$m range.

The first and second solid phases of the mixed-bed solid phase of the present invention can be solid or semi-solid, porous, or non-porous. Selection of such properties of each of the solid phases used in the mixed-bed solid phase of the present invention is largely determined by the nature of the target nucleic acid, and by the nature of the material from which it is to be isolated. When pores are present in any of the solid phases in the mixed bed solid phase, at least some of the pores are preferably of a size sufficiently large to admit the target nucleic acid material into the interior of the solid phase particle.

The silica magnetic particles may contain substances, such as transition metals or volatile organics, which could adversely affect the utility of target nucleic acids substantially contaminated with such substances. Such contaminants can affect downstream processing, analysis, and/or use of target nucleic acids contaminated therewith. For example, such contaminants can nick or degrade the target nucleic acids, or inhibit the activity of enzymes added to the target nucleic acids. Any such substances present in the silica magnetic particles used in the present invention are preferably present in a form which does not readily leach out of the particle and into the isolated biological target material produced according to the methods of the present invention. Iron is one such undesirable contaminant, particularly when the biological target material is a target nucleic acid.

Iron, in the form of magnetite, is present at the core of a particularly preferred form of the silica magnetic particles of the present invention. Iron has a broad absorption peak between 260 and 270 nanometers (nm). Target nucleic acids have a peak absorption at about 260 nm, so iron contamination in a target nucleic acid sample can adversely affect the accuracy of the results of quantitative spectrophotometric analysis of such samples. Any iron containing silica magnetic particles used to isolate target nucleic acids using the present invention preferably do not produce isolated target nucleic acid material sufficiently contaminated with iron for the iron to interfere with spectrophotometric analysis of the material at or around 260 nm.

The most preferred silica magnetic particles used in the methods and materials of the present invention (i.e., SOCM particles), leach no more than 50 ppm, more preferably no more than 10 ppm, and most preferably no more than 5 ppm of transition metals when assayed as follows. Specifically, 0.33 g of the particles (oven dried @ 110° C.) into 20 ml of 1N HCl aqueous solution (using de-ionized water). The resulting mixture is then agitated only to disperse the particles. After about 15 minutes total contact time, a portion of the liquid from the mixture is then analyzed for metals content. Any conventional elemental analysis technique may be employed to quantify the amount of transition metal in the resulting liquid, but inductively coupled plasma spectroscopy (ICP) is preferred.

At least two commercial silica magnetic particles are particularly preferred for use as the first or second silica matrices in the present invention, BioMag® Magnetic Particles from PerSeptive Biosystems, and MagneSil™ particles available from Promega Corporation. Any source of magnetic force sufficiently strong to separate the silica magnetic particles from a solution would be suitable for use in the present invention. However, the magnetic force is preferably provided in the form of a magnetic separation stand, such as one of the MagneSphere® Technology Magnetic Separation Stands (Cat. No.'s Z5331 to 3, or Z5341 to 3) from Promega Corporation.

Target nucleic acids are inherently negatively charged at any pH above pH 2, and can, therefore, reversibly bind to ion-exchangers which are positively charged, at any pH above pH 2. Note that some ion-exchangers have an overall positive charge at one pH, where it can act as an anion-exchanger, and an overall neutral or negative charge at another pH. Such ion-exchangers are only capable of exchanging ions with a target nucleic acid at a pH and other conditions where the ion-exchanger acts as an anion-exchanger. Capacity for exchange with a target nucleic acid varies widely from one ion-exchanger to another. At least one of the solid phases in the mixed-bed solid phase preferably has an ion-exchange residue capable of exchanging with the target nucleic acid covalently attached to the surface of the support material, either directly, or through an intermediary. The term "surface", as used herein, refers to the portion of the support material of a solid phase which comes into direct contact with a solution when the solid phase is combined therewith. Suitable anion-exchange solid phases for use in the mixed-bed solid phases of the present invention are commercially available.

The ion-exchange solid phase is preferably a solid support, such as Sepharose® (Pharmacia), polystyrene, or a silica based material, with an ion-exchange group covalently attached thereto. The ion-exchange group comprises at least one ion-exchange residue, which is capable of acting as an anion-exchanger, wherein the ion-exchange residue is covalently attached to the solid support directly, or through a hydrocarbon linker. When a hydrocarbon linker is present, it preferably includes at least one residue which can act as a cation exchanger at a pH which is not within the range of pH at which the ion-exchange residue is positively charged. An ion-exchange solid phase with such a linker is referred to herein as a "mixed-mode" solid phase. See U.S. patent application Ser. No. 09/312,172 for an invention titled pH DEPENDENT ION EXCHANGE MATRIX AND METHOD OF USE IN THE ISOLATION OF NUCLEIC ACIDS, filed on May 14, 1999 for further information about particularly preferred mixed-mode solid phases suitable for use in nucleic acid isolation, incorporated by reference herein.

Regardless of whether a mixed-mode or single mode ion-exchange solid phase is used in the present invention, the preferred properties of the ion-exchange residue of the ion exchange group are the same. The ion-exchange residue preferably has the capacity to exchange readily with the target nucleic acid of interest under solution conditions wherein the target nucleic acid is not chemically degraded (e.g. It is known that RNA degrades in the presence of strongly alkaline solutions, i.e. solutions with pH of 10 or greater, while DNA is stable in such solutions. It is also known that DNA degrades in the presence of concentrated chaotropic agent solutions, such as solutions containing at least 2M guanidine thiocyanate while RNA is stable at guanidine thiocyanate concentrations between 2 and 5M). See, e.g., U.S. Pat. No. 5,346,994.

The ion exchange group attached to the ion exchange solid phase is most preferably selected from the group consisting of dimethyl-amine, histamine, ethanolamine, histidine, pyridylalanine, and pyridylcysteine. Note that the last two preferred ion exchange groups listed above are mixed-mode ion-exchange groups, shown below in a configuration wherein each is covalently attached to a different solid phase. The wavy line in the figures below represents the solid phase, such as a silica magnetic particle, to which each of the ion exchange groups is attached:

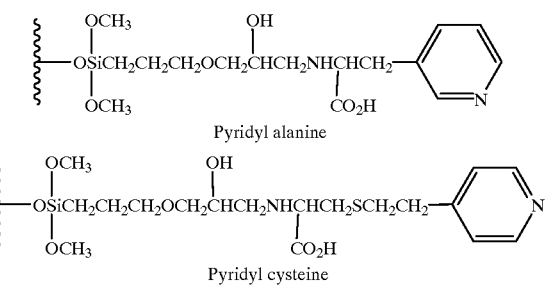

The capacity of the first or second solid phase to bind to or exchange with a target nucleic acid under any given solution conditions is a function of functional groups at the surface of the solid phase, whether on the outer surface or lining the exterior surface of pores extending therefrom into each particle of solid phase. When the solid phase is an anion-exchange solid phase, the target nucleic acid reversibly binds to the anion-exchange functional groups on the surface of the solid phase, under solution conditions (particularly, pH and salt) in which the anion-exchange group is sufficiently charged to exchange ions with the target nucleic acid.

Anion-exchange solid phases suitable for use in the mixed-bed solid phases of the present invention are commercially available, particularly in the form of non-magnetic solid phases. See, e.g. DEA-Sepharose™, Q-Sepharose™, and DEAE-Sephadex™ from Pharmacia (Piscataway, N.J.), Dowex® I from The Dow Chemical Company (Midland, Mich.), Amberlite® from Rohm & Haas (Philadelphia, Pa.), Duolite® from Duolite International, In. (Cleveland, Ohio), Dialon TI, and Dialon TII. Anion exchange solid phases suitable for use in the present invention can also be synthesized by covalently attaching any suitable anion-exchange residue to one of the suitable support material described above, using conventional synthetic organic chemistry. For example, a suitable anion-exchange solid phase can be produced by covalently attaching a dimethyl-amine residue to a silica based material, such as a silica gel particle or magnetic silica particle, by reacting the silica based material with 3-(diethylamino) propyl trimethoxysilane in the presence of dichloromethane and tributylamine. W. Jost, et al., *J. Chromatog.* 185 (1979) 403–412. Other anion-exchange residues, such as histidine, can be similarly attached to silica based materials to produce suitable anion-exchange solid phases.

The first solid phase and second solid phase of the mixed-bed solid phase of this invention are selected for their capacity to bind and release a target nucleic acid of interest under different solution conditions, such that the first solid phase binds the target nucleic acid in the presence of a first solution and releases it in the presence of a second solution, while the second solid phase binds the target nucleic acid in the presence of the second solution and releases the target nucleic acid in the presence of the first solution. The composition of the first and second solution depends upon the nature of the functional groups at the surface of the first and second solid phases, respectively. For example, when the functional group of the first solid phase is an anion-exchanger, then the first solution contains a sufficiently high salt concentration to provide the ions needed for an ion exchange reaction but not a sufficiently high salt concentration to interfere with the exchange of ions between the anion-exchange groups of the solid phase and the target nucleic acid. The pH of the first solution must also be at or below the pKa for the anion-exchange group of a first anion exchange solid phase to ensure the anion-exchange group has a sufficiently positive charge to exchange with the target nucleic acid.

When the first solid phase is an anion-exchange solid phase and the second solid phase is also an anion exchange solid phase, the pKa of the anion-exchange group of the second solid phase preferably differs from that of the first solid phase by at least 0.5 pKa units, more preferably by at least 1 pKa unit, and most preferably by at least 2 pKa units. The first anion-exchange solid phase and the second anion-exchange solid phase can also differ further from one another in capacity to bind the target nucleic acid of interest, due to differences in charge and/or anion-exchange group density at the surface of each such solid phase.

FIG. 1 illustrates a theoretical solid phase mix of a first anion-exchange solid phase and a second anion-exchange solid phase of the present invention, and the selection of first solution, second solution, and elution solution for use in the isolation of a target nucleic acid in accordance with the method of the present invention. Specifically, FIG. 1 shows the relative capacities of two different solid phases, A and B, to bind and release a target nucleic acid (RNA or DNA) under various salt and pH conditions. Solid phase A has a pKa of 7.0, while solid phase B has a pKa of 8.5. Solid phase A also differs from solid phase B in its charge density at different pH's. Specifically solid phase A has a higher positive charge density than B in the presence of a solution pH of less than 6.0 and a lower positive charge density than B in the presence of a solution pH of greater than 6.0. Solid phase A binds to the target nucleic acid at solution pH and salt concentrations which fall below the A line (dashed) in FIG. 1, and releases target nucleic acid bound thereto at pH and salt concentrations above that same line. The B line (dotted) in FIG. 1 similarly shows the pH and salt concentrations at which solid phase B binds to (below the line) or releases (above the line) the target nucleic acid. Such binding calibration curves can be constructed readily, using standard binding capacity studies.

Solid phase calibration curves, such as the one illustrated in FIG. 1, can be used to select the optimal conditions for the first solution, second solution, and elution solutions used in the method of isolating target nucleic acids of the present invention. A circle, labeled "solution #1" in FIG. 1 shows solution conditions at which solid phase A will bind to the target nucleic acid, while solid phase B will release any target nucleic acid bound thereto. The pH of solution #1 is selected to be as close as possible to a neutral pH while optimizing the difference in binding and releasing capacity of solid phases A and B. The circle labeled solution #2 is similarly selected for binding to solid phase B and release from solid phase A in a pH range as close as possible to neutral pH. The elution solution composition can be selected from any salt concentration and pH mixture above that of both lines A and B in FIG. 1. But, the pH is preferably at about 7 and the salt concentration is preferably as low as possible.

One can switch the solution conditions of a theoretical mixture of solid phase A, solid phase B, and the target nucleic acid back and forth between solutions #1 and #2 multiple times to remove non-target nucleic acid impurities from the mixture before eluting the target nucleic acid therefrom.

When either the first solid phase or the second solid phase is not an anion-exchange solid phase, it is preferably a solid phase material with functional groups on the surface capable of binding directly to the target nucleic acid of interest through interactions other than through ion-exchange such as hydrophobic interaction, reverse-phase interaction, nucleic acid hybridization, or Hoogsteen base pairing. In this embodiment of the invention, the first or second solid phase of the mixed-bed solid phase is a silica based solid phase material, more preferably a silica material having a siliceous oxide coating. When the silica based solid phase is a silica material with a siliceous oxide coating, the solid phase is characterized by having silanol groups at the surface of the silica material. Silanol groups are known to releasibly bind target nucleic acids by reversed phase interactions. McLaughlin, L. M., *Chem Rev* (1989) 89: 309–319, at p. 309. A particularly preferred embodiment of the mixed-bed solid phase described immediately above, the embodiment comprising an anion exchange solid phase and a silica based solid phase, is referred to herein as "silica/IE mixed-bed solid phase".

The silica/IE mixed-bed solid phase is used to isolate a target nucleic acid using the method of the present invention, wherein the mixed-bed solid phase is combined with a first solution followed by a second solution, as described above. One solution promotes binding with the silica solid phase, while the other promotes binding with the ion exchange solid phase. Either solution can be used as the first solution, provided the other solution is the second solution.

Either the first solution or the second solution preferably contains at least 100 mM, more preferably at least 250 mM, and even more preferably at least 500 mM concentration of a chaotropic agent. The chaotropic agent is preferably a guanidine salt, more preferably guanidine thiocyanate. Target nucleic acids bind to a silica-based solid phase material readily in the presence of chaotropic agents, but are readily released therefrom in the presence of a solution, which is substantially free of chaotropic agents. The term "substantially free", as used herein means that the concentration of chaotropic agents in a solution in contact with the silica based mixed bed solid phase is sufficiently low that the second solid phase preferentially forms a complex with endotoxins in the solution, and releases any target nucleic acid bound to the other solid phase in the silica/IE mixed-bed solid phase.

When one solution with the characteristics described above is selected for use as the first or second solution to be used in the present method, the other (i.e., second or first) solution has the following characteristics. The solution is preferably substantially free of chaotropic agents. The pH and salt composition of the solution are preferably selected for their capacity to facilitate the exchange of ions between the target nucleic acid and the anion-exchange group of the first solid phase. The salt concentration is preferably as low as possible to ensure release of the target nucleic acid from the silica-based solid phase.

When the target nucleic acid isolated according to the present method is RNA, the composition of this solution is preferably a composition, which allows the target RNA, but not DNA to bind to the ion exchange solid phase. More preferably, the composition of this solution promotes binding of the target RNA to at least one solid phase of the mixed-bed solid phase.

When the target nucleic acid isolated according to the present method is DNA, the composition of this solution is preferably a composition which allows the target DNA but not RNA to bind to the ion exchange solid phase. More preferably, the composition of this solution promotes binding of the target DNA to the ion exchange solid phase, but not to the silica-based solid phase component of the silica/IE mixed-bed solid phase. Even more preferably, the composition of the solution promotes binding of endotoxins to the mixed-bed solid phase, more preferably to the silica based solid phase component of a silica/IE mixed-bed solid phase.

The silica/IE mixed-bed solid phase of the present invention described immediately above is particularly well suited for use in isolating a target nucleic acid from endotoxins in a mixture thereof. Specifically, combination of such a mixed-bed solid phase with a mixture of endotoxins and the target nucleic acid in the presence of a first solution which is substantially free of chaotropic agents, will cause the target nucleic acid to bind to the one solid phase by anion-exchange and the endotoxins to bind to the other solid phase. Endotoxins tend to bind to silica based solid phases, in solutions which are substantially free of chaotropic agents. The binding of endotoxins to such solid phases is so tight that addition of solutions containing chaotropic agents to such a solid phase mixture does not appear to result in the release of endotoxins therefrom. Endotoxins can be removed from silica surfaces, such as those found on siliceous oxide coated silica magnetic particles, by washing with water.

When the method of the present invention is used to isolate a target nucleic acid from a mixture of the target nucleic acid and at least one contaminants, either the first or second solution can be combined with the mixed-bed solid phase in the presence of the target nucleic acid mixture in the first step. The solution used first determines which solution is used in the next step. Specifically, if the first solution is combined with the mixed-bed solid phase first, the second solution is combined therewith next, and vice versa. After the initial combining step, the mixed-bed solid phase is separated from the initial solution and combined with the other solution. The combining and separation steps are preferably repeated until the mixed-bed solid phase has been combined with and separated from each of the first and second solutions at least twice. At each change from the first to the second solution, at least 90% of the target nucleic acid remains bound to the mixed-bed solid phase, while at least one contaminants are removed therefrom.

Depending upon the composition of the first and second solutions, it is contemplated that the method of the present invention will further comprise a step of washing the mixed-bed solid phase between solution addition steps and/or after separation from the final solution and prior to the elution step. Wash steps are particularly preferred, after contact with a first or second solution containing a chaotropic agent (e.g., GTC) prior to contact with a first, second, or elution solution which is substantially free of chaotropic agents. The composition of any such wash buffer is selected to ensure the target nucleic acid remains bound to the mixed-bed solid phase. Water is preferably used to wash the mixed-bed solid phase of a first anion-exchange solid phase and second silica based solid phase illustrated above, to ensure complete removal of chaotropic agent after addition of the second solution thereto.

The first solution, second solution, and any wash solution are all preferably prepared from or consist of distilled, deionized, or nanopure water. The term "nanopure water" as used herein refers to water purified with an ultrafiltration system which produces water of comparable quality to a Nanopure® Filtration System. The distilled, deionized, or nanopure water can be autoclaved or filtered prior to use in the method. However, during such additional processing steps, impurities can be introduced into the water, such as a weak buffer of greater than pH 5.0. Such impurities can raise the pH of the water to such an extent that it can cause target nucleic acids, particularly amplified nucleic acids (e.g., PCR amplified DNA), to be released from a mixed-bed resin when placed into contact therewith. When the target nucleic acid is RNA, any water placed into direct contact with the mixed-bed solid phase must be substantially RNAse free.

Elution of the target nucleic acid from the mixed-bed solid phase is carried out in the presence of an elution buffer selected for its capacity to ensure the release of the target nucleic acid from the mixed-bed solid phase. The target nucleic acid eluted from the mixed-bed solid phase in the final step of the method is sufficiently pure to be used in applications sensitive to contamination with endotoxins and other at least one contaminants, applications including transfection of tissue culture cells.

The following, non-limiting examples teach various embodiments of the invention. In the examples, and elsewhere in the specification and claims, volumes and concentrations are at room temperature unless specified otherwise. Only the magnetic silica particles, particularly the siliceous oxide coated silica magnetic particles such as those described above and immediately below, were used in the examples below. However, one skilled in the art of the present invention will be able to use the teachings of the present disclosure to select and use silica matrices other than silica magnetic particles, and silica magnetic particles other than the specific types of particles used in the illustrations of the methods of the present invention demonstrated in the Examples, below. The Examples should not be construed as limiting the scope of the present invention.

The silica magnetic particles used in each of the Examples below were selected from either of two batches of particles. Both batches of silica magnetic particles were found to produce acceptable results when tested as described below. One of the two batches of particles used below had the following physical characteristics: surface area of 55 m$^2$/g, pore volume of 0.181 ml/g for particles of <600 Å diameter, pore volume of 0.163 ml/g for particles of >600 Å diameter, median particle size of 5.3 µm, and iron leach of 2.8 ppm when assayed as described herein above using ICP. The other batch of silica magnetic particles used below was found to have the following characteristics: surface area of 49 m$^2$/g, pore volume of 0.160 ml/g (<600 Å diameter), pore volume of 0.163 ml/g (>600 Å diameter), median particle size of 5.5 µm, and iron leach of 2.0 ppm.

The Examples below describe procedures used to produce two different mixed bed solid phases of magnetic particles, methods used to isolate plasmid or genoric DNA from various media using the mixed bed solid phase particles, and results of various assay results done on samples of nucleic acids eluted from the mixed bed solid phase particles.

EXAMPLE 1

Gel Electrophoresis Assays

Samples of target nucleic acids isolated according to procedures described in Examples below were analyzed for contamination with non-target nucleic acids, and for size as follows. The samples were fractionated on an agarose gel of appropriate density (e.g., a 0.7% agarose gel was used to analyze plasmid DNA, while a 1.5% agarose gel was used to analyze RNA). The fractionated nucleic acid was visualized using a fluorescent label or by dying the gel with a DNA sensitive stain, such as ethidium bromide or silver staining. The resulting fractionated, visualized nucleic acid, was either photographed or visualized using a fluorimager and the resulting image printed out using a laser printer.

In some cases, size standards were fractionated on the same gel as the target nucleic acid, and used to determine the approximate size of the target nucleic acid. In every case where a gel assay was done, the photograph or fluorimage of the fractionated nucleic acid was inspected for contamination by non-target nucleic acids. For example, images of fractionated samples of plasmid DNA were inspected for RNA, which runs considerably faster than DNA on the same gel, and for chromosomal DNA, which runs considerably slower than plasmid DNA on the same gel. Images of isolated plasmid DNA were also inspected to determine whether most of the plasmid DNA shown in the image is intact, supercoiled, plasmid DNA.

EXAMPLE 2

Absorption Spectrophotometry

Samples of target nucleic acids isolated from various media, as described below, were also analyzed using absorption spectrophotometry. Absorption measurements were taken at wavelengths of 260, 280, and 230 nanometers (nm). $A_{260}/A_{280}$ absorption ratios were computed from the measurements. An $A_{260}/A_{280}$ of greater than or equal to 1.80 was interpreted to indicate the sample analyzed therein was relatively free of protein contamination. The concentration of nucleic acid in each sample was determined from the absorption reading at 260 nm ($A_{260}$).

EXAMPLE 3

Endotown Assays

A limulus amoebocyte lysate (LAL) gel precipitation assay, was conducted to determine the number of units of endotoxin in bacteria lysate samples taken before and after the lysate solutions came into contact with one or more of the silica matrices tested in Examples below. E-TOXAT®, from SIGMA® (St. Louis, Mo., cat. no. 210-D1) was used as the amoebocyte lysate standard for this series of LAL assays. E-TOXATE® is described in the 1997 SIGMA® Catalog (p. 448) as "(Amoebocyte lysate; Horseshoe crab lysate) from *Limulus polyphemus*". Endotoxin-free water ("ETF water") was used in all the steps of this assay, including all the dilution steps. Each sample or set of samples was assayed according to the following procedure:

1. Samples were prepared for serial dilution, with a larger initial dilution factor used (e.g., 1:10000 or higher) for samples which had not been in contact with any endotoxin removal agent, such as silica gel particles, and with smaller initial dilutions of 1:500 to 1:1000 for samples which had come into contact with such agents. Endotoxin-free ("ETF") water was used for all dilutions described herein.

2. 2×Serial dilutions were prepared of each sample as follows: 25 µl of each sample added to 25 µl of ETF water in the first set of wells of 96 well microtiter plate, and mixed by pipetting. 25 µl of that diluted solution was then transferred to a second well with another 25 µl of ETF water, and so on until a series of 12 samples has been prepared per sample.

3. A series of dilutions of endotoxin standard were prepared as follows. First, the contents of a fresh bottle of Endotoxin Standard (SIGMA® cat. no. 210-SE) were diluted with ETF water, in accordance to the manufacturer's instructions on the bottle. Second, the following volumes of ETF water were added to each of a series of nine (9) 1.5 ml microcentrifuge tubes as follows: 900 µl to tubes 1–3, 1,050 µl to tube 4, and 500 µl to tubes 5–9. Third, 100 µl of the Endotoxin Standard from the bottle diluted as described above was transferred to tube 1, mixed, and then serially diluted as follows:

100 µl from tube 1 was added to tube 2 and mixed, for 40 Endotoxin Units ("EU") per milliliter (ml.), 100 µl from tube 2 was added to tube 3 and mixed, for 4 EU/ml, 150 µl from tube 3 was added to tube 4 and mixed, for 0.5 EU/ml, 500 µl from tube 4 was added to tube 5 and mixed, for 0.25 EU/ml, 500 µl from tube 5 was added to tube 6 and mixed, for 0.125 EU/ml, 500 µl from tube 6 was added to tube 7 and mixed, for 0.06 EU/ml, 500 µl from tube 7 was added to tube 8 and mixed, for 0.03 EU/ml, 500 µl from tube 8 was added to tube 9 and mixed, for 0.015 EU/ml.

4. The Endotoxin Standards diluted as described above and a blank standard were then transferred to a microtiter plate as follows: 25 µl ETF water (blank) in column 1, 25 µl from standard tube 4 in column 2, 25 µl from standard tube 5 in column 3, 25 µl from standard tube 6 in column 4, 25 µl from standard tube 7 in column 5, 25 µl from standard tube 8 in column 6, and 25 µl from standard tube 9 in column 7.

5. A fresh bottle of E-TOXATE®, i.e. LAL in lyophilized form, was opened for every two microtiter plates of samples or standards to be tested. ETF water was added to each bottle of E-TOXATE® to a final concentration contains, and an amount of ETF water was added to each bottle to bring about 5 ml of ETF water was added to each bottle. When multiple bottles of E-TOXATE® were opened for a single set of assays, the bottle contents were resuspended in ETF water, as described immediately above, and combined prior to use. 25 µl of E-TOXATE® was added to each well of each microtiter plate containing a sample, standard, or blank.

6. Once E-TOXATE® had been added to each well, the microtiter plate was covered, and the plate placed in a 37° C. incubator for 1 hour (+/−5 minutes), during which time the E-TOXATE solution will gel in the presence of a sufficiently high amount of endotoxin.

7. The microtiter plate was then removed from the incubator, examined for gelation, and the last well in each column with gelation (i.e. positive result) was noted. The following formula was used to determine the EU/ml of the original sample tested in each column:

EU/ml=1/(highest dilution of sample which tests positive)×(highest dilution of standard which tests positive)

For example, if the sample was positive (i.e. gel found) at a dilution of 1/4000, but was negative (i.e. no gel found) at a dilution of 1/8000, and the standard was positive at 0.06 dilution and negative at 0.03, then the EU/ml is determined as follows: EU/ml=1/(1/4000)×0.06=240 EU/ml.

EXAMPLE 4

Transfection Assay

DNA isolated according to procedures described below was also used to transfect HeLa cells, a human ovarian cancer cell line. The cells were cultured in Dulbecco's Modified Eagles Medium (DMEM) plus 10% fetal bovine serum—10% $CO_2$. The cells were plated in 24 well dishes in appropriate media and the following procedure was followed.

1. The cells were placed in 24 well dishes, about 50,000 cells per well, approximately 24 hours before initiating transfection.

2. On the day of transfection, the media was removed from each well and replaced with fresh growth media (+serum) within one to three hours before initiating transfection.

3. A mixture of each of the four Samples of DNA (Samples 1–4) was prepared as follows. Enough mixture of each sample of DNA was prepared to transfect six wells of cell culture, as follows. 6 µl (about 6 µg) of DNA, 23.8 µl of calcium chloride, and 160 µl of sterile water were combined in a sterile polystyrene tube. The DNA/$CaCl_2$ mixture prepared above was added, dropwise, to 190.2 µl of Hank's Buffered Saline (HBS), while gently vortexing the HBS.

4. The HBS/DNA/$CaCl_2$ mixture was incubated for 30 minutes at room temperature, before adding 54.6 µl of the mixture to each well of cells. The mixture was added directly to the media containing serum.

5. The plates of treated cells were then returned to the incubator. The cells were fed with fresh serum the next day, using the same serum composition used in step 2, above.

6. After 48 hours, the cells were harvested by removing the growth medium and adding 100 µl of cell culture lysis reagent per well.

Cells transfected and harvested as described above were then assayed to see whether the reporter gene, in this case the luciferase gene of pGL3 plasmid DNA, was expressed in the cells. A standard luciferase assay, the Luciferase Assay System commercially available from Promega Corporation, was used to detect and quantify luciferase expression in the cells.

Cells harvested in step 6, above, were incubated for another 15 minutes at room temperature before being assayed for luciferase expression. An aliquot from each well of cells was then placed in a different well of a microtiter plate dish. The amount of luminescence emanating from each well was detected and quantified using a luminometer.

EXAMPLE 5

Synthesis of Anion Exchange Magnetic Silica Particles

A diethylamino (DEA) anion exchange residue was covalently attached to MagneSil™ Particles through a propyl dimethoxy silane ligand according to the following synthesis procedure:

1. MagneSil™ particles were activated by drying at 120° C. in a vacuum oven overnight. 2. 4.25 grams of the activated MagneSil™ particles were combined with 2.5 ml. of [3-(diethylamino)propyl]trimethoxysilane (96% from Aldrich®) and 17.5 ml of dichloromethane (Aldrich®). 3 to 4 drops of tributylamine(Aldrich®) were then added to the resulting mixture.

3. The reaction mixture was shaken at room temperature for 2 days. At the end of that incubation period, the solution was separated from the particles by filtration.

4. The particles/filtrate were then washed five times with 75 ml of dichloromethane, followed by two washes with 100 ml of water.

5. An aliquot of the washed particles was dried in an oven for use in the target nucleic acid binding studies illustrated in Example 5, below.

The DEA-magnetic silica particle synthesis reaction used in this example is further illustrated by the reaction diagram below:

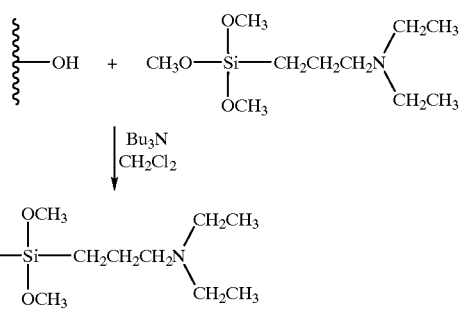

EXAMPLE 6

Preparation of Cleared Lysate of Bacteria Cells Transformed with plasmid DNA

*E. coli* bacteria cells, DH5α strain, were transformed with pGL3-Control Vector (Promega) plasmid DNA, and grown in an overnight culture of Luria Broth ("LB") medium at 37° C., then harvested by centrifugation. The following solutions were used to prepare a lysate of the harvested cells, as described below:

Cell Resuspension Solution:
50 mM Tris-HCl, pH 7.5
10 mM EDTA
100 µg/ml DNase-free ribonuclease A (RNase A)
Wizard® Neutralization Solution:
1.32M KOAc (potassium acetate), pH 4.8
5 Neutralization Solution
1.69M K$^+$/2.26M GTC/6.5M Acetate, pH 4.18
Cell Lysis Solution:
0.2M NaOH
1% SDS (sodium dodecyl sulfate)

A cleared lysate of the transformed cells was produced as follows:

1. The cells from 10 ml of bacteria culture were harvested by centrifuging the culture for 1–2 minutes at top speed in a microcentrifuge. The harvested cells were resuspended in 250 µl of Cell Resuspension Solution, and transferred to a microcentrifuge tube. The resulting solution of resuspended cells was cloudy.
2. 250 µl of Cell Lysis Solution was then added to the solution of resuspended cells and mixed by inversion until the solution became relatively clear, indicating the resuspended cells had lysed.
3. 350 µl of Neutralization Solution (Wizard® or #5, as indicated below) was added to the lysate solution, and mixed by inversion. The lysate became cloudy after the Neutralization Solution was added.
4. The solution was then spun in a microcentrifuge at top speed for 5 minutes to clear the lysate.
5. The resulting supernatant of cleared lysate was transferred to a new microcentrifuge tube.

Cleared lysate solutions from step 5 were pooled, and then exposed to either of two magnetic silica solid phases or to a mixture of the two solid phases under various solution conditions designed to promote adherence of plasmid DNA to either or both solid phases, as described in Examples 4–6 below. The mixed-bed solid phase was then washed, and plasmid DNA eluted therefrom as described below. Each eluent was tested for endotoxins according to Example 3, and for yield and quality of the plasmid DNA contained therein according to the procedures described in Example 1 and 2.

EXAMPLE 7

Isolation of Plasmid DNA from Cleared Lysate Using Silica/IE-DEA Mixed Bed Solid Phase, Silica Magnetic Particles, or IE-DEA Silica Magnetic Particles a. Starting Materials and Solution Compositions Plasmid DNA was isolated from a bacteria lysate prepared as described in Example 6, by binding to and eluting plasmid DNA contained therein from either silica magnetic particles, DEA-silica magnetic particles prepared as described in Example 4, or a mixture of the two types of particles, as follows. The mixture of silica magnetic particles and DEA-silica magnetic particles used in this Example are referred to herein as "Silica/DEA Mixed Bed" particles. The single particle binding and elution procedures were included as controls.

The following solutions were used as described below:
Wash Solution A:
0.74 M K$^+$/0.29M Acetate, pH 4.0
1.0M Guanidine thiocyanate (GTC)

Wash Solution B:
0.37M K$^+$/0.1 2M Acetate, pH 4.0
0.43M Guanidine thiocyanate
Elution Buffer:
2.0M NaCl
200 mM Tris-HCl, pH 7.3 b. Control 1: Plasmid DNA Isolated from Lysate with GTC, Using Silica Magnetic Particles The first control sample of plasmid DNA was isolated from a lysate solution using the silica magnetic particles alone, as follows. The lysate was prepared according to Example 4, using #5 Neutralization Solution (i.e. Neutralization Solution with 2.26M GTC). 150 µl MagneSil® particles suspended in water, for a final concentration of 100 mg of particles per ml, were added to 250 µl of the lysate and then removed from the lysate using magnetic force. The particles were then suspended in and removed from 1.0 ml of 0.85M GTC by magnetic force twice. After the second removal step, the particles were suspended and removed from 1.0 ml of Wash Solution A three times. The washed particles were then dried in a vacuum centrifuge (a SpeedVac). Finally, the dried particles were suspended in 80 µl of water for five minutes, and removed from the resulting eluent by centrifugation for 10 minutes at 12,000 g in a microfuge.

c. Control 2: Plasmid DNA Isolated from Lysate with no GTC, Using DEA-Silica Magnetic Particles As another control, plasmid DNA was isolated from DEA-magnetic silica particles synthesized as described in Example 4, above, according to the following procedure. The lysate was prepared according to Example 1, using Wizard® Neutralization Solution (i.e. Neutralization Solution with no GTC). 150 µl of DEA-silica magnetic particles (suspended in water for a 100 mg/ml concentration) were added to 250 µl of the lysate and then removed from the lysate using magnetic force. The particles were then resuspended one time in 1.0 ml of Wash Solution B, followed by three resuspensions in 1.0 ml water, wherein magnetic force was used to remove the particles from the wash solution after each resuspension step. Finally, the dried particles were suspended in 300 µl of Elution Buffer for five minutes, and removed from the resulting eluent by centrifugation for 10 minutes at 12,000 g in a microfuge.

d. WIZ-Samples: Plasmid DNA Isolated from Lysate with GTC, Using Silica/IE-DEA Mixed-Bed Solid Phase Plasmid DNA was isolated from lysate prepared as described in Example 6, using Wizard® Neutralization Solution (no GTC) using a mixed-bed solid phase of 15 mg of the silica magnetic particles and 30 mg of the DEA-silica magnetic particles (water was removed from the mixed-bed solid phase particles prior to lysate addition), as follows:

1. The lysate was combined with 15 mg MagneSil™ and 30 mg DEA-magnetic silica particles, mixed and separated therefrom by magnetic force. The lysate was discarded.
2. The particles were resuspended in 950 µl of Wash Solution B, mixed, and separated therefrom by magnetic force. This step was repeated twice, discarding the wash solution after each separation step.
3. The particles were resuspended in 950 µl of 2M GTC, and separated therefrom by magnetic force. This step was repeated once, and the GTC solution discarded after each separation step.
4. The particles were resuspended in 950 µl of 0.85M GTC, and separated therefrom by magnetic force. This step was repeated once, and the GTC solution discarded after each separation step.
5. The particles were resuspended in 950 µl of water, and separated therefrom by magnetic force. This step was repeated once, and the water discarded after each separation step.

6. Steps 2–5 were repeated once.

7. The particles were resuspended in 300 µl of Elution Buffer, for five minutes, and removed from the resulting eluent by magnetic force.

e. #5-Samples: Plasmid DNA Isolated from Lysate with no GTC, Using Silica/IE-DEA Mixed-Bed Solid Phase Plasmid DNA was also isolated from lysate prepared as described in Example 6, using #5 Neutralization solution, using the silica/IE-DEA Mixed-Bed solid phase, as follows:

1. The lysate was combined with 15 mg silica magnetic particles and 30 mg DEA-silicamagnetic particles, mixed and separated therefrom by magnetic force. The lysate was discarded.

2. The particles were resuspended in 950 µl of water, mixed, and separated therefrom by magnetic force. This step was repeated once, discarding the water wash solution after each separation step.

3. The particles were resuspended in 950 µl of Wash Solution B, and separated therefrom by magnetic force. This step was repeated three times, and the GTC solution discarded after each separation step.

4. The particles were resuspended in 950 µl of 2M GTC, and separated therefrom by magnetic force. This step was repeated once, and the GTC solution discarded after each separation step.

5. The particles were resuspended in 950 µl of 0.85M GTC, and separated therefrom by magnetic force. This step was repeated once, and the GTC solution discarded after each separation step.

6. The particles were resuspended in 950 µl of water, and separated therefrom by magnetic force. This step was repeated once, and the water discarded after each separation step.

7. Steps 2–6 were repeated once.

8. The particles were resuspended in 300 µl of Elution Buffer, for five minutes, and removed from the resulting eluent by magnetic force.

f. Precipitation of Plasmid DNA in Test and Control Samples

Plasmid DNA was precipitated out of each control and test sample of eluent produced as described above, as follows. 800 µl of 95% ethanol was combined with each 300 µl sample of eluent, and stored at −20° C. for 60 hours in a microcentrifuge tube. The resulting DNA precipitate was then spun out of solution by centrifugation for 10 minutes at 12,000 g in a microcentrifuge. The ethanol supernatant was discarded, and the pellet washed with 500 µl of 70% ethanol. The second ethanol wash solution was similarly removed by centrifugation, and the pellet dried. The resulting pellet of DNA was then resuspended in 80 µl ETF water.

EXAMPLE 8

Results from Spectrophotometric Assay of Plasmid DNA Isolated from Lysate Using Silica Magnetic Particles, DEA-Silica Magnetic Particles, or Silica/ IE-DEA Mixed Bed Solid Phase Each of the samples eluted from the single particle type controls or from the mixed-bed solid phase as described in Example 7, above, was analyzed using the spectrophotometric assay procedure described in Example 2, above. The assay results are Shown in Table 1, below:

TABLE 1

| Sample Tested | $A_{260}$ | $A_{260}/A_{280}$ | Total Amt. of nucleic acid, in µg |
|---|---|---|---|
| Control 1: Eluent from Silica Magnetic Particles + lysate in #5, after 1X washes in Wash Solution A | 0.590 / 0.517 | 1.85 / 1.89 | 47.26 / 41.41 |
| Control 2: Eluent from DEA-Silica Magnetic Particles + lysate in WIZ, after 1X washes in Wash Solution B | 0.747 / 0.787 | 1.78 / 1.77 | 59.80 / 63.00 |
| WIZ-1: Eluent from Silica/DEA Mixed-Bed Particles + lysate in WIZ, after 1X washes in Wash Solution B | 0.997 / 1.225 | 1.84 / 1.86 | 79.78 / 98.07 |
| WIZ-2: Eluent from Silica/DEA Mixed-Bed Particles + lysate in WIZ, after 1X washes in Wash Solution B, and 1X washes in 2M GTC. | 1.533 / 1.677 | 1.84 / 1.83 | 122.66 / 134.22 |
| WIZ-3: Eluent from Silica/DEA Mixed-Bed Particles + lysate in WIZ, after 2X washes in Wash Solution B, and 1X washes in 2M GTC. | 0.900 / 0.998 | 1.81 / 1.80 | 72.00 / 79.88 |
| WIZ-4: Eluent from Silica/DEA Mixed-Bed Particles + lysate in WIZ, after 2X washes in Wash Solution B, and 2X washes in 2M GTC. | 0.893 / 0.867 | 1.79 / 1.75 | 71.47 / 69.39 |
| #5-1: Eluent from Silica/DEA Mixed-Bed Particles + lysate in #5, after 1X washes in Wash Solution B. | 0.869 / 0.717 | 1.74 / 1.76 | 69.57 / 57.37 |
| #5-2: Eluent from Silica/DEA Mixed-Bed Particles + lysate in #5, after 1X washes in Wash Solution B, and 1X of washes in 2M GTC. | 0.908 / 0.850 | 1.77 / 1.76 | 72.72 / 68.04 |
| #5-3: Eluent from Silica/DEA Mixed-Bed Particles + lysate in #5, after 2X washes in Wash Solution B, and 1X washes in 2M GTC. | 0.841 / 0.815 | 1.79 / 1.77 | 67.32 / 65.23 |
| #5-4: Eluent from Silica/DEA Mixed-Bed Particles + lysate in #5, after 2X washes in Wash Solution B, and 2X washes in 2M GTC. | 0.803 / 0.752 | 1.70 / 1.67 | 64.26 / 60.19 |

The results in Table 1 show that a larger amount of DNA was isolated from lysate in the Wizard® Neutralization Solution ("WIZ", above) or lysate in the #5 Neutralization Solution ("#5", above), using Mixed-Bed resin, than was isolated therefrom using either the MagneSil™ particles or the DEA-MagneSil™ particles alone (Controls 1 and 2, respectively, above). All the eluents tested were fairly pure, (i.e., with a an absorbance ratio of $A_{260}/A_{280}$ of about 1.8). Eluents from Control 1 (i.e., eluents of the MagneSil™ particles, alone), and WIZ-1 through 3 (i.e., eluents of Mixed-Bed particles from lysate solutions in WIZ) were highly pure, with $A_{260}/A_{280}$ ratios of over 1.80. The highest yield of DNA was obtained in the WIZ-2 samples, wherein the samples tested were eluted from the Silica/DEA Mixed Bed particles after exposure of the particles to lysate in WIZ, followed by washes in each of two different solutions (Wash Solution B and 2M GTC).

EXAMPLE 9

Results of Assay of Endotoxins and Transfection Efficiency of Plasmid DNA Isolated from Lysate in Example 7

The same control and test samples assayed in Example 8 were also assayed for endotoxin contamination according to the procedure described in Example 3, above, and for transfection efficiency according to the procedure described in Example 4, above. Both sets of assay results are shown in Table 2, below:

TABLE 2

| Sample Tested | Endotoxins (EU/ml) | % Transfected |
|---|---|---|
| Control 1: Eluent from Silica Magnetic Particles + lysate in #5, after 1X washes in Wash Solution A | >128,000<br>>128,000 | 83<br>43 |
| Control 2: Eluent from DEA-Silica Magnetic Particles + lysate in WIZ, after 1X washes in Wash Solution B | 2,000<br>2,000 | 156<br>232 |
| WIZ-1: Eluent from Silica/DEA Mixed-Bed Particles + lysate in WIZ, after 1X washes in Wash Solution B | 500<br>500 | 64<br>54 |
| WIZ-2: Eluent from Silica/DEA Mixed-Bed Particles + lysate in WIZ, after 1X washes in Wash Solution B, and 1X washes in 2M GTC. | 250<br>250 | 231<br>321 |
| WIZ-3: Eluent from Silica/DEA Mixed-Bed Particles + lysate in WIZ, after 2X washes in Wash Solution B, and 1X washes in 2M GTC. | 500<br>250 | 60<br>98 |
| WIZ-4: Eluent from Silica/DEA Mixed-Bed Particles + lysate in WIZ, after 2X washes in Wash Solution B, and 2X washes in 2M GTC. | 250<br>500 | 120<br>113 |
| #5-1: Eluent from Silica/DEA Mixed-Bed Particles + lysate in #5, after 1X washes in Wash Solution B. | 32,000<br>32,000 | 214<br>167 |
| #5-2: Eluent from Silica/DEA Mixed-Bed Particles + lysate in #5, after 1X washes in Wash Solution B, and 1X of washes in 2M GTC. | 16,000<br>8,000 | 240<br>121 |
| #5-3: Eluent from Silica/DEA Mixed-Bed Particles + lysate in #5, after 2X washes in Wash Solution B, and 1X washes in 2M GTC. | 32,000<br>32,000 | 177<br>238 |
| #5-4: Eluent from Silica/DEA Mixed-Bed Particles + lysate in #5, after 2X washes in Wash Solution B, and 2X washes in 2M GTC. | 8,000<br>8,000 | 165<br>174 |

The results in Table 2, above, show that each Control-1 eluent was highly contaminated with endotoxins. All the WIZ samples showed very low endotoxin activity unit values (EU/ml of less than 1,000), and reasonably high transfection efficiencies (% transfection of at least 50%). All the #5 samples, above had slightly higher endotoxin levels. But, the transfection efficiencies for all the #5 samples exceeded 100%.

EXAMPLE 10

Production of Silica/IE-Histidine Mixed Bed Solid Phase

A second silica/ion exchange mixed bed solid phase was produced, as follows, for use in the additional nucleic acid isolation examples, below. (i.e., Examples 11 to 12). The second silica/ion exchange mixed bed was produced by combining equal amounts of the same type of silica magnetic particles used above with ion exchange silica magnetic particles, wherein the ion exchange particles are silica magnetic particles with histidine residues covalently attached thereto (hereinafter, "IE-His particles"). For the Examples below, 50 $\mu$l of a 100 mg/ml solution of the silica magnetic particles was combined with 50 $\mu$l of a 100 mg/ml solution of the IE-His particles. The resulting mixture is referred to herein as the "Silica/His Mixed Bed" solid phase.

The IE-His particles used to make the Silica/His Mixed Bed solid phase were produced using a silica activation and ligand attachment procedure substantially similar to the procedure used to produce the IE-DEA silica magnetic particles in Example 5, above. Histidine was selected as a ligand because of its known properties as an excellent anion exchanger in the neutral to basic pH range.

EXAMPLE 11

Isolation of Plasmid DNA from Agarose, Using Silica/IE-HIS Mixed Bed Solid Phase Silica/IE-His Mixed Bed Solid Phase prepared as described in Example 10, above, were used to extract and isolate plasmid DNA from bands of the DNA cut from an agarose gel, as described herein below. As a control, plasmid DNA was also extracted from bands of the same DNA cut from the same agarose gel, using silica magnetic particles, as described below.

Figure 2:
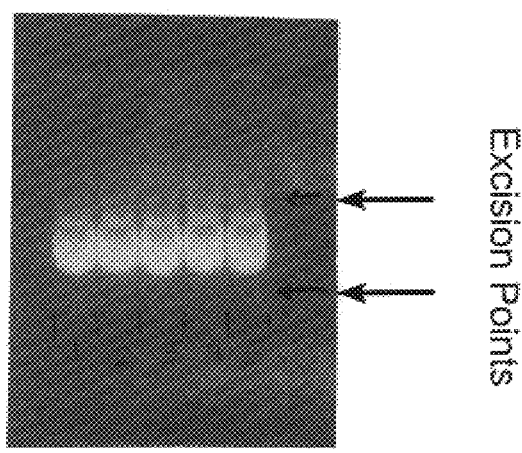
FIG. 2 is a copy of a photograph of plasmid DNA fractionated on an agarose gel and stained with ethidium bromide, with arrows showing the points at which the bands of plasmid DNA were excised from the gel prior to isolation of the plasmid DNA therefrom with mixed-bed solid phase particles, as described in Example 11.

Plasmid DNA was fractionated on an agarose gel and excised therefrom, as follows. 20 $\mu$g of pGL3 plasmid DNA was aliquoted into each of five different wells of a 1% agarose gel, and electrophoresed for a sufficient amount of time to clearly separate plasmid DNA from chromosomal or RNA contaminants in each lane. The gel was then stained with ethidium bromide, and the bands visualized under ultraviolet light. The bands were individually excised from the gel (band weight ranged from 0.51 g. to 0.56 g per slice). FIG. 2 shows the agarose gel and excision points from which the plasmid DNA bands were excised from the gel.

Once excised from the gel, each band was dissolved in 550 $\mu$l of a GTC Buffer (4.0 M GTC, 1.7 M Na$^+$, and 2.6 M Acetate; pH 5.35) through 30 minutes of incubation at 65 °C. When the gel slices were completely dissolved, 500 $\mu$l of the resulting liquid from each dissolved band was transferred to a tube containing either 50 $\mu$l of magnetic silica particles, or 100 $\mu$l of Silica/IE-His Mixed Bed Solid Phase, and plasmid DNA extracted therefrom as described below.

The control sample tube of dissolved gel slices mixture and silica magnetic particles, prepared as described above, was processed as follows:

1. The control sample was incubated for 20 minutes at room temperature, resuspending the silica magnetic particles in the mixture twice midway through the incubation period.
2. The silica magnetic particles were then removed from all liquid in the incubation mixture, by magnetic force.
3. The silica magnetic particles were then washed three times with 500 $\mu$l of 70% ethanol added to the particles in each wash step. Magnetic force was used to remove the wash solution from the silica magnetic particles, after each addition of ethanol wash solution.
4. The silica magnetic particles were allowed to air dry for at least 15 minutes after the final wash and magnetic separation step.
5. DNA was eluted from the silica magnetic particles with 100 $\mu$l of 10 mM Tris Buffer (pH 8.7). The resulting eluent was separated from the particles by centrifugation.

The test sample tube of dissolved gel slices mixture and Silica/IE-His Mixed Bed Solid Phase particles, prepared as described above, was processed as follows:

1. The tube of control sample was incubated for 20 minutes at room temperature, resuspending the mixed-bed particles in the mixture twice midway through the incubation period.
2. The silica magnetic particles were then removed from all liquid in the incubation mixture, by magnetic force.
3. The silica magnetic particles were then washed three times with 500 $\mu$l of Nanopure Water added per tube.

Magnetic force was used to remove the wash solution from the silica magnetic particles, after each wash step.

4. DNA was eluted from the mixed-bed particles with 100 μl of 10 mM Tris Buffer (pH 8.7). The resulting eluent was separated from the particles by centrifugation.

The control and test sample eluents produced as described above were then tested for yield and purity, using the spectrophotometric analysis procedure set forth in Example 2, above. Both the yield and purity of plasmid DNA were higher in the test sample, the eluent from the mixed-bed solid phase. Specifically, the $A_{260}$ for the control sample (i.e., the eluent from the silica magnetic particles, alone) was measured at 0.0104, while the $A_{260}$ for the test sample (i.e., the eluent from the Silica/IE-His Mixed Bed) was measured at 0.0166. Thus, the $A_{260}$ results indicated that a significantly higher yield of plasmid DNA was recovered from the agarose samples compared to the control. The control sample $A_{260}/A_{280}$ was measured at 1.54, while the test sample $A_{260}/A_{280}$ was found to be 1.89. Thus, the absorbance ratio results indicated, furthermore, that the plasmid DNA isolated from the agarose using the mixed-bed solid phase was of a higher purity than plasmid DNA isolated from the agarose using silica magnetic particles, alone.

EXAMPLE 12

Isolation of A Fragment of Lambda DNA from Agarose, Using Silica/IE-HIS Mixed Bed Solid Phase vs. Using Silica Magnetic Particles, Alone Two aliquots of equal amounts of lambda DNA/ Hind III markers (Promega Cat. No. G1711) loaded on the same 1% agarose gel, and electrophoresed until all the different sized fragments of DNA in the markers were completely separated. The band in each of the two marker lanes corresponding to a molecular weight of 4,361 was then excized. The starting amount of lambda DNA fragment in the excized band was about 306 mg. 306 μl of a GTC Buffer (4.0M GTC/0.34 M Na$^+$/ 0.52M Acetate, pH5.3) was combined with each excized band in a separate tube, and incubated for 30 minutes at 65° C. to dissolve the gel. When the gel slices were completely dissolved, 250 μl of the liquid from one sample was transferred to a tube containing 50 μl of 100 mg/ml silica magnetic particles, the control sample. A mixed bed resin test sample was made by transferring 250 μl of the liquid from the other sample to a tube containing 100 μl of 100 mg/ml silica/IE-His Mixed Bed Solid Phase.

Samples of lambda DNA from the excized band were extracted from the test and control samples, prepared as described above, using the same protocols used to isolate plasmid DNA from the test and control samples in Example 10, above.

The resulting samples of lamba DNA eluted from the two different types of resins were of comparable yield and purity, when tested by spectophotometric analysis according to Example 2 and by gel electrophoresis according to Example 1.

EXAMPLE 13

Isolation of Amplified DNA from an Agarose Gel, Using Silica/IE-HIS Mixed Bed Solid Phase Silica/IE-His mixed bed solid phase prepared as described in Example 10, above, was also used to isolate a 1.8 Kb fragment of DNA amplified using a polymerase chain reaction (PCR) from an agarose gel. The following process was used to isolate the fragment of interest from the gel:

1. A reaction mixture from the amplification of a 1.8 Kb sequence of an *Adenometous polyposis coli* (APC) gene was fractionated on an agarose gel, and a band corresponding in size to the 1.8 Kb fragment was excized therefrom. The excised band weighed 725 mg.

2. 725 μl of a GTC Buffer (4.0M GTC, 1.7M Na$^+$, and 2.1M Acetate, pH 5.35) was added to the excised band, and incubated at 65° C. until the agarose gel dissolved.

3. 400 μl aliquots of the resulting solution were transferred to three separate tubes containing 10 mg of silica/IE-His mixed bed solid phase particles, prepared as described in Example 10, above.

4. The resulting mixture of particles and solution was allowed to stand at room temperature for 15 minutes, to ensure binding of DNA in the mixture to the particles. At the end of that period, the solution was removed from the particles, using magnetic force.

5. Each sample of particles was then washed three times with one of the following wash solutions: (1) nanopure water (unbuffered, purified water, with a pH of less than 5.0); (2) 0.2 mM KOAc pH 4.8 prepared with nanopure water; or (3)1.3 mM KOAc, pH 4.8 prepared with nanopure water. Magnetic force was used to separate the particles from the wash solution after each wash step.

Figure 5:
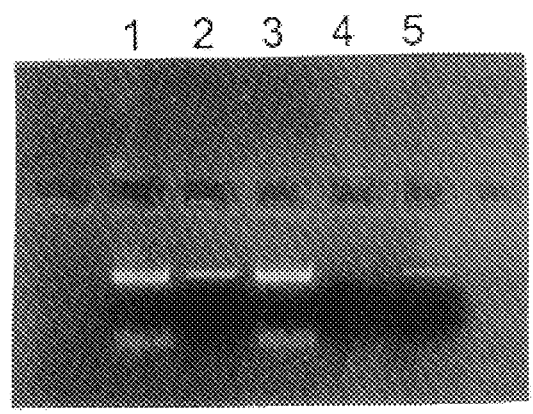
FIG. 5 is a copy of a photograph of DNA amplified with the polymerase chain reaction (PCR) and isolated using a mixed-bed solid phase under various wash conditions, and stained with ethidium bromide.

6. 50 μl of 10 mM Tris-HCl, pH 8.0 was added to each sample of particles to elute DNA therefrom, and separated from the particles, by magnetic force. 20 μl of the eluent from each sample of particles was loaded on an agarose gel, along with two aliquots of the reaction mixture from step 1, above, and fractionated by gel electrophoresis. FIG. 5 is a photograph of the gel, after it was stained with ethidium bromide, and illuminated under ultraviolet light. The lanes of the gel shown in FIG. 5 were loaded as follows:

1. PCR reaction mixture
2. Nanopure water wash of silica/IE-His mixed bed particles
3. PCR reaction mixture
4. 0.2 mM KOAc, pH 4.8 wash of silica/IE-His mixed bed particles
5. 1.3 mM KOAc, pH 4.8 wash of silica/IE-His mixed bed particles FIG. 5 shows that the samples in lanes 1–3 and 5 all contained the expected band at about 1.8 Kb. However, the band in lane 5 was considerably less intense than that in lane 2, and no band was visible in lane 4. It appears the nanopure water worked best at washing the particles, without eluting the DNA therefrom in step 5, above.

EXAMPLE 14

Preliminary Isolation of Total RNA and Genomic DNA from Mouse Blood

Genomic DNA and total RNA were partially isolated from mouse blood from Lampire Biological Laboratories (Pipersville, Pa.), using reagents from an SV Total RNA Isolation System (Promega, cat. no. Z3100), as follows. The resulting mixture of genomic DNA and total RNA was then further processed to isolate genomic DNA therefrom, using three different substrates and protocols, according to the procedures of Examples 15 to 17, below. Total RNA could also be isolated from the mixture of genomic DNA and total RNA produced as described herein, according to the procedure of theoretical Example 19, below.

The following solutions were used in the present preliminary isolation procedure:

SV RNA Red Blood Cell Lysis Solution
  5 mM $MgCl_2$
  10 mM NaCl
  10 mM Tris-HCl (pH 7.0)
SV RNA Lysis Buffer
  4M GTC
  0.01M Tris (pH 7.5)
  0.97% β-Mercaptoethanol
SV RNA Wash Solution
  60 mM Potassium Acetate
  10 mM Tris-HCl (pH 7.5 at 25 C.)
  60% Ethanol (% by volume)
SV RNA Dilution Buffer
  17.5% NaCl
  8.8% Sodium citrate, pH 7.0
  10% SDS (saturated)
  10% F, D&C Blue #1

(% quantities above are all percent by weight, except where indicated otherwise.)

A mixture of partially isolated total RNA and genomic DNA was produced from samples of the mouse blood cells, as follows:

1. 1.0 ml of mouse whole blood cells was aliquotted into each of twelve microfuge tubes.
2. The cells in each tube were pelleted by centrifugation at 4,000 rpm for 2 minutes. The plasma supernatant was removed with a pipette, and discarded.
3. 1 ml. of SV RNA Red Blood Cell Lysis Solution was added to the harvested cells, and the cells resuspended in the Lysis Solution by pipetting or by gentle vortexing.
4. The resuspended cell/lysis solution mixture was centrifuged at 4,000 rpm for 2 minutes. The resulting supernatant was removed with a pipette and discarded, leaving behind a white blood cell pellet and a pellet of erythrocyte debris above the white cells. Liquid was removed from the microcentrifuge tube caps during this step and all remaining steps of this procedure.
5. Steps 3 and 4 were repeated twice, for a total of three times. For blood volumes greater than 600 μl, 200 μl of the erythrocyte debris was removed, leaving several hundred microliters of erythrocyte debris in the tube.
6. The cell pellet was vortexed for 5 seconds on a high speed setting, to resuspend the white cells and the erythrocyte debris.
7. 175 μl of SV RNA Lysis Buffer was added to the cells, and the cells vortexed again at high speed for 5 seconds.
8. 350 μl of SV RNA Dilution Buffer was added to each tube of lysed cells, and vortexed again at a high speed for 5 seconds.
9. The tubes of lysed and diluted cells were then centrifuged at 12,000 to 14,000 rpm for 10 minutes at 20 to 25° C.
10. The supernatant was transferred to a sterile microfuge tube containing 150 μl 95%–100% ethanol, where upon DNA in the resulting mixture formed a precipitate. The mixture was then mixed by inversion until all precipitated DNA went back into solution.

EXAMPLE 15

Isolation of Genomic DNA Using an SV RNA Spin Basket

Three samples of the supernatant/ethanol mixture from step 10 of Example 14 were transferred to separate sterile SV RNA Spin Baskets, each of which was placed inside a fresh collection tube. The resulting assemblies were incubated at room temperature for 5 minutes. The following procedure was then followed to isolate genomic DNA from the mixture, using the spin basket assembly:

1. The spin basket assembly was spun in a microfuge at 12,000 to 14,000 for 10 seconds. The contents of the collection tube were discarded, the spin basket reinserted into the collection tube, and spun again for another 10 seconds. The contents of the collection tube were, again, discarded.
2. 700 μl of 70% ethanol in water was placed into the spin basket, and the spin basket/collection tube assembly spun at 12–14K for 10 seconds. The resulting flow through was discarded.
3. The empty spin basket was spun again at 12 to 14K for 20 seconds to remove residual wash solution from the basket.
4. Finally, the spin basket was placed into a sterile microfuge tube, and 100 μl of 50 mM Tris-HCl buffer, pH 9.5 was added to the spin basket to elute any genomic DNA bound thereto. The spin basket was incubated for 5 minutes at room temperature, then spun in a microfuge at 12 to 14K for ten seconds. The spin basket was then removed from the microfuge tube of eluent, and the eluent saved for testing as described in Example 18, below, along with the samples of genomic DNA isolated according to the isolation procedures described in the next two examples, below.

EXAMPLE 16

Isolation of Genomic DNA Using Silica Magnetic Particles

Three samples of the supernatant/ethanol mixture from step 10 of Example 14 were transferred to separate microfuge tubes, each of which contained 50 μl 100 mg/ml of silica magnetic particles alone (i.e., not in a mixed-bed configuration). The tubes were incubated at room temperature for 5 minutes, resuspending the particles in the mixture twice about half-way through the incubation period. The following procedure was then followed to isolate genomic DNA from other materials in the mixture:

1. Magnetic force was used to separate the silica magnetic particles from the liquid portion of the mixture, after the incubation period was over. The liquid was discarded.
2. The silica magnetic particles were then washed four times with 1 ml of 70% ethanol. The ethanol wash solution was separated from the silica magnetic particles by magnetic force. The wash solution was discarded after each wash step.
3. The silica magnetic particles were allowed to dry in the microcentrifuge tube at room temperature until the ethanol had evaporated therefrom.
4. Finally, 100 μl of 50 mM Tris-HCl buffer, pH 9.5 was added to the silica magnetic particles after the last wash step, and incubated for 5 minutes at room temperature. The buffer/particle mixture was then spun in a microcentrifug at 12 to 14K for ten seconds. The eluent was removed from the resulting pellet of silica magnetic particles, and set aside for testing with the other samples as described in Example 17, below.

EXAMPLE 17

Isolation of Genomic DNA from Mouse Blood Using Silica/IE-HIS Mixed-Bed Solid Phase Six samples of the ethanol/mouse blood lysate mixture from step 10 of Example 14 were transferred to separate microcentrifuge tubes, each of which contained 50 µl 100 mg/ml of Silica/IE-His Mixed Bed Solid Phase particles. The tubes were incubated at room temperature for 5 minutes, resuspending the particles in the mixture twice about halfway through the incubation period. The following procedure was then followed to isolate genomic DNA from other materials in the mixture:

1. Magnetic force was used to separate the mixed-bed solid phase particles from the liquid portion of the mixture, after the incubation period was over. The liquid was discarded.
2. Three of the samples of mixed-bed solid phase particles separated from the supernatant/ethanol mixture in step 1, above, were washed once with 1.0 ml of Wash Solution A (66 mM KOAc, pH 4.8; 500 mM NaCl), while the remaining three samples were washed once with 1.0 ml of Wash Solution B (66 mM KOAc, pH 5.8, with no NaCl added). Magnetic force was used to separate the mixed-bed solid phase particles from the wash solution. The wash solution was discarded.
3. The mixed-bed solid phase particles were then washed four times with 1.0 ml each of nanopure water, separating the water from the mixed-bed solid phase particles after each wash step by magnetic force. The wash solution was discarded after each wash step.
4. Finally, 100 µl of 50 mM Tris-HCl buffer, pH 9.5 was added to the mixed-bed solid phase particles after the last wash step, and incubated for 5 minutes at room temperature. The buffer/particle mixture was then spun in a microcentrifuge at 12 to 14K for ten seconds. The eluent was removed from the resulting pellet of silica magnetic particles, and set aside for testing with the other samples as described in Example 18, below.

EXAMPLE 18

Assay of Genomic DNA Eluted from SV RNA Spin Basket, Silica Magnetic Particles, and Silica/IE-HIS Mixed-Bed Solid Phase Genomic DNA eluted from each of the isolation means used in Examples 15–17, above was tested, using spectrophotometry as described in Example 2. The results of this assay are presented in Table 3, below:

TABLE 3

| Solid Phase & Wash Solution | $A_{230}$ | $A_{260}$ | $A_{260}/A_{280}$ | Total DNA Isolated | Ave. DNA Isolated |
|---|---|---|---|---|---|
| Silica Magnetic Particles, with 70% Ethanol used in Wash | 0.604 | 0.142 | 1.80 | 7.11 µg | 6.61 µg |
|  | 0.500 | 0.135 | 1.80 | 6.80 µg |  |
|  | 0.335 | 0.118 | 1.74 | 5.92 µg |  |
| Silica/IE-His Mixed Bed, with Wash Solution A (with salt) | 0.199 | 0.183 | 1.71 | 9.15 µg | 10.03 µg |
|  | 0.222 | 0.229 | 1.75 | 11.46 µg |  |
|  | 0.773 | 0.189 | 1.84 | 9.49 µg |  |
| Silica/IE-His Mixed Bed, with Wash Solution B (no salt added) | 0.198 | 0.200 | 1.83 | 10.00 µg | 9.96 µg |
|  | 0.200 | 0.201 | 1.82 | 10.06 µg |  |
|  | 0.175 | 0.196 | 1.85 | 9.80 µg |  |
| SV RNA Spin Basket, with 70% Ethanol Wash | 0.133 | 0.234 | 1.81 | 11.62 µg | 12.55 µg |
|  | 0.128 | 0.232 | 1.82 | 11.59 µg |  |
|  | 0.154 | 0.288 | 1.89 | 14.38 µg |  |

The results in Table 3, above, show that mouse genomic DNA of comparably high purity and yield was obtained using each of the procedures described in Examples 15–17 to isolate the DNA from the same mixture of DNA and RNA produced from the same amount (1 ml) of mouse blood, according to the lysis and preliminary isolation procedure of Example 14. Specifically, the $A_{260}/A_{280}$ ratio for each of the samples tested fell within the range between 1.70 and 1.90, the expected range for genomic DNA which is relatively free of protein contamination.

Absorbance readings were also taken of each sample at 230 mn in order to detect carry over of guanidine used in each isolation procedure into the each final sample of genomic DNA isolated therewith. The $A_{230}$ results are shown in Table 3, above. One can see that the lowest $A_{230}$ readings were obtained from the samples of genomic DNA isolated using the SV RNA Spin Basket, and those isolated using the Mixed-Bed Solid Phase and Wash Solution B (no salt), indicating the lowest amount of guanidine carry over in those two sets of samples. However, all the $A_{230}$ readings set forth in Table 3, above, are low enough to indicate that all the samples isolated above are substantially pure.

In other words, the $A_{230}$ results obtained herein show that all the means for removing guanidine from the solid support used to isolate genomic DNA prior to elution of the DNA therefrom were approximately equally effective. However, two of the isolation methods used to obtain the samples tested herein required time consuming evaporation or extra centrifugation steps prior to DNA elution to ensure removal of guanidine from the solid support used in each such method. See, e.g., evaporation during spin step 3 with empty spin basket in Example 15, and evaporation of wash solution from particles in step 3 of Example 16. Contrastingly, no such evaporation step was used prior to elution of the genomic DNA from the mixed-bed solid phase, in accordance with the isolation procedure described in Example 16, above. Specifically, in that particular example, the aqueous wash solutions combined with and removed from the mixed-bed solid phase prior to the elution step dissolved and removed residual guanidine therefrom.

EXAMPLE 19

Preparation of a Mixture of Ethanol and Cleared Lysate of Mouse Liver Tissue for Use as a Substrate in the Isolation of Total RNA with Various Isolation Means A mixture of ethanol and a cleared lysate of mouse liver tissue was prepared according to the tissue lysate preparation procedure set forth in the SV Total RNA Isolation System Technical Manual (Promega, TM #48), as follows:

1. Three mouse livers were homogenized in the presence of SV RNA Lysis Buffer, combining 171 mg of liver tissue to each milliliter of Lysis Buffer. Homogenization was continued until lysis was complete (i.e., until no visible tissue fragments remained in the solution).
2. 175 µl of the lysate was transferred to each of six 1.5 ml microcentrifuge tubes. 350 µl of SV RNA Dilution Buffer (blue) (See Example 14) was added to each tube. The contents of each microcentrifuge tube were mixed by inversion. The diluted lysate was then placed in a water bath or heating block at 70° C., and incubated for about 3 minutes.
3. All the samples of diluted lysate were then centrifuged at about 12,000 to 14,000×g for 10 minutes, producing a cleared lysate supernatant.
4. Each supernatant of cleared lysate (about 500 µl) was transferred to a fresh microcentrifuge tube, by pipetting, and 200 µl of 95% ethanol was added to each sample of cleared lysate. The resulting ethanol/lysate mixture was mixed by pipetting.

EXAMPLE 20

Isolation of Total RNA from Ethanol/Lysate of Mouse LiverS, Using Porous and Non-Porous Silica/IE-HIS Mixed-Bed Solid Phase Total mouse RNA was then isolated from four samples of the ethanol/lysate mixture prepared from mouse livers, as described in Example 19, above, using two different mixed-bed solid phases. One of the two mixed-bed solid phases was a silica/IE-His mixed-bed solid phase of porous silica magnetic particles, prepared as described in Example 10, above. The other mixed-bed solid phase used herein was prepared in the same way as the porous silica/IE-His mixed-bed solid phase, except that non-porous silica magnetic particles were used instead of porous particles. The same procedure was used to isolate total RNA from each sample using both types of mixed-bed solid phases.

Each sample of the ethanol/lysate mixture was transferred to a microcentifug tube containing 50 µl each of 100 mg/ml of either porous or non-porous silica/IE-His mixed bed solid phase particles. The mixture and particles were incubated at room temperature for 5 minutes, resuspending the mixed bed solid phase particles in the mixture twice about half-way through the incubation period. RNA was then isolated from the mixed-bed solid phase according to the following procedure:

1. Magnetic force was used to separate the mixed-bed solid phase particles from the supernatant/ethanol mixture. The liquid separated therefrom was discarded.
2. 50 µl of a mixture of DNase I enzyme in DNase Buffer (0.0225 M Tris (pH 7.5), 1.125 M NaCl, and 0.09 M $MnCl_2$) was added directly to the mixed-bed solid phase particles, and incubated for 15 minutes at 20–25° C. At the end of the incubation period, 200 µl of SV DNase Stop Solution (60 mM potassium acetate, 10 mM Tris-HCl, pH 7.5 at 25° C., and 60% ethanol) was added to each sample.
3. The particles were separated from the DNase incubation solution by magnetic force, and the solution discarded.
4. 1.0 ml of Wash Solution B (66 mM KOAc, pH 5.8) was added to each sample, and magnetic force was used to separate the mixed-bed solid phase particles from the wash solution. The wash solution separated therefrom was discarded.
5. The mixed-bed solid phase particles were washed four times with 1.0 ml each of nanopure water, separating the water from the mixed-bed solid phase particles after each wash step by magnetic force. The wash solution separated therefrom was discarded after each wash step.
6. Finally, 100 µl of nuclease free water was added to the mixed-bed solid phase particles after the last wash step, and incubated for 5 minutes at room temperature. The water/particle mixture was spun in a microcentrifuge at 12 to 14K for ten seconds. The resulting eluent was removed from the resulting pellet of silica magnetic particles, and tested as described in Example 22, below.

EXAMPLE 21

Isolation of Total RNA from Ethanol/Lysate of Mouse Livers, Using SV RNA Spin Basket Assembly Total mouse RNA was then isolated from the remaining two samples of the ethanol/lysate mixture prepared from mouse livers, as described in Example 19, above, using an isolation procedure described in the SV Total RNA Isolation System Technical Manual (TM #48, Promega Corp.), as follows:

1. Each of the two samples of supernatant/ethanol mixture was transferred to an SV RNA Spin Basket, and centrifuged with a Collection Tube at 12,00–14,000×g for about one minute. The solution collected in the Collection Tube was discarded.
2. 50µl of a mixture of DNase I enzyme in DNase Buffer (0.0225 M Tris (pH 7.5), 1.125 M NaCl, and 0.09 M $MnCl_2$) was added directly to each Spin Basket after the separation step described above. The resulting mixtures were incubated for 15 minutes at 20–25° C. After the incubation, 200 µl of SV DNase Stop Solution (60 mM potassium acetate, 10 mM Tris-HCl, pH 7.5 at 25° C., and 60% ethanol) was added to each sample.
3. 600 µl of SV RNA Wash Solution, with ethanol added, was added to the sample in each Spin Basket. The Spin Basket was centrifuged with a Collection Tube again at 12,000–14,000×g for about one minute, and the contents of the Collection Tube discarded.
4. Wash step 3, above, was repeated using 250 µl of SV RNA Wash Solution, and high speed centrifugation for two minutes.
5. Finally, 100 µl of nanopure, Nuclease-Free water was added to each isolation means to elute total RNA therefrom. The eluent was separated from each of the isolation means by centrifugation.

EXAMPLE 22

Figure 3:
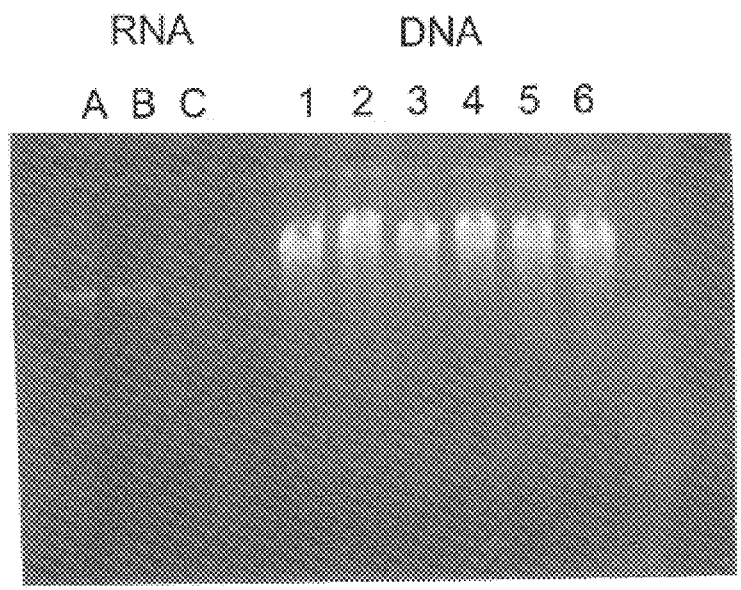
FIG. 3 is a copy of a photograph of genomic DNA and total RNA isolated from mouse blood using a mixed-bed solid phase, as described in Examples 14, 17, and 18, fractionated on an agarose gel, and stained with ethidium bromide.

Comparison of DNA and Total RNA Isolated from Mouse Blood Using Silica/IE-HIS Mixed Bed Solid Phase 20 µl of each sample of genomic DNA and total RNA isolated from mouse blood with silica/IE-HIS mixed bed solid phase as described in Examples 17 and 21, respectfully, were fractionated on an agarose gel, and stained with ethidium bromide. A photograph of the gel is reproduced in FIG. 3. The lanes of the gel were loaded as follows:

Lanes A, B, and C were loaded with isolated total RNA

Lanes 1–3 were loaded with DNA isolated using Wash Solution A

Lanes 4–6 were loaded with DNA isolated using Wash Solution B.

From the gel assay results, it appears intact RNA and DNA were isolated from mouse blood, although the amount of RNA isolated was small by comparison to the DNA. It also appears that DNA isolated with either Wash solution used in step 2 was substantially intact, and appeared to be free of contamination with RNA.

EXAMPLE 23

Assay of Total Mouse RNA Eluted from Porous Silica/IE-HIS Mixed-Bed Solid Phase, Non-Porous Silica/IE-HIS Mixed-Bed Solid Phase, and SV RNA Spin Basket Assembly Total mouse RNA eluted from each of the isolation means used in Examples 19–21, above, was analyzed using gel electrophoresis as follows. 10 µl of each sample was loaded into a separate well of a 1.5% agarose gel, with samples eluted from the same isolation means loaded in pairs separated by a 100 bp DNA ladder (Promega Cat. No. G2101) was loaded into the empty well between each pair of samples. The 1.5% agarose gel was then electrophoresed for a sufficient amount of time to provide clear separation between the rungs of the 100 bp ladder. Finally, the agarose gel was stained with ethidium bromide, and photographed under ultraviolet light.

Figure 4:
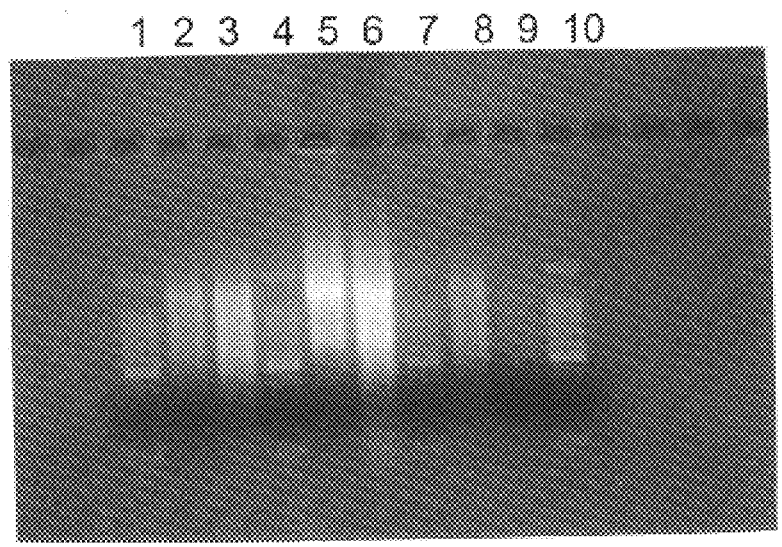
FIG. 4 is a copy of a photograph of total RNA isolated from mouse liver, using a mixed-bed solid phase or using an SV Total RNA Isolation System® (Promega Corp.), fractionated on an agarose gel with several samples of a 100 bp ladder, and stained with ethidium bromide.

FIG. 4 is a copy of the photograph of the 1.5% agarose gel of the samples and ladders loaded and fractionated as described above. The following samples were loaded onto each lane of the gel shown in FIG. 4:

Lane 1: Promega 100 bp DNA ladder
Lanes 2 & 3: Eluent from porous silica/IE-His mixed bed solid phase
Lane 4: 100 bp DNA ladder
Lanes 5 & 6: Eluent from SV RNA Spin Basket
Lane 7: 100 bp DNA ladder
Lanes 8 & 9: Eluent from non-porous silica/IE-His mixed bed solid phase
Lane 10: 100 bp DNA ladder The results of this assay showed that all three isolation means and methods used in Examples 19–21, above, produced what appears to be intact RNA. FIG. 4 also indicates that at least one of the two eluents from one of the SV RNA Spin Baskets was contaminated with a high molecular weight nucleic acid, probably genomic mouse DNA. See the band just under the well in Lane 4. None of the samples of total RNA isolated with porous or non-porous mixed bed solid phase particles appear to contain any such contaminants.

FIG. 4 shows that magnetic separations and the mixed bed isolation procedures of the present method can be used to isolate total RNA which is at least as free from contaminants as that produced using SV RNA Spin Baskets. However, unlike the SV RNA isolation procedure used in Example 21, above, the present method (see, e.g. Example 20, above) requires no spins in a centrifug, and no ethanol washes (just water washes).

Obviously, many modifications and variations of the invention as hereinbefore set forth may be made without departing from the spirit and scope thereof. Therefore, only such limitations should be imposed as are indicated in the claims, below.

What is claimed is:

1. A method of isolating a target nucleic acid from a mixture comprising the target nucleic acid and at least one contaminant, comprising:
   a) providing a mixed-bed solid phase comprising a first solid phase and a second solid phase, wherein:
      the first solid phase has the capacity to bind to the target nucleic acid in a first solution and to release the target nucleic acid bound thereto in the presence of a second solution,
      the second solid phase has the capacity to bind to the target nucleic acid in the second solution and to release the target nucleic acid bound thereto in the presence of the first solution, and
      the first solid phase and the second solid phase each have the capacity to release the target nucleic acid bound thereto in the presence of an elution buffer;
   b) combining the mixture with the mixed-bed solid phase in the presence of the first solution and permitting the target nucleic acid to bind to the first solid phase;
   c) separating the mixed-bed solid phase from the first solution;
   d) combining the mixed-bed solid phase with the second solution, and permitting the target nucleic acid to release from the first solid phase and bind to the second solid phase;
   e) separating the mixed-bed solid phase from the second solution; and
   f) combining the mixed-bed solid phase with the elution buffer, and permitting the target nucleic acid to release from the mixed-bed solid phase into the elution buffer.

2. The method of claim 1, wherein the mixed-bed solid phase provided in step (a) is equilibrated with an equilibration buffer which is substantially free of chaotropic agents prior to combining the equilibrated mixed-bed solid phase with the mixture in step (b).

3. The method of claim 1, wherein at least one removing step selected from steps (d) and (f) is done using a solution removal means selected from the group consisting of decantation, direct removal under a vacuum, centrifugation, filtration, gravity flow through a column, and high pressure flow through a column.

4. The method of claim 1, wherein the first solid phase and the second solid phase are both magnetic particles, and magnetic force is used to retain mixed-bed solid phase in a container during at least one removing step selected from steps (d) and (f).

5. The method of claim 4, wherein the first solid phase is a silica magnetic particle and the second solid phase comprises a silica particle with an anion exchange group covalently attached thereto, wherein the anion exchange group is capable of exchanging with the target nucleic acid.

6. The method of claim 5, wherein the anion exchange group is selected from the group consisting of an amine, a dimethyl-amine, a histamine, a di-ethanolamine, a histidine, a pyridyl alanine, and a pyridyl cysteine.

7. The method of claim 5, wherein the first solution has a pH of at least about 4 and up to about 9 and a salt concentration of at least about 100 mM and up to about 3M; and wherein the second solution has a pH of at least about 4 and up to about 9 and a salt concentration of at least 0.5M and up to about 4.0M.

8. The method of claim 5, wherein the first solution has a pH of at least about 4 and up to about 9 and a salt concentration of at least about 100 mM and up to about 3M; and wherein the second solution has a pH of at least about 4 and up to about 9 and a salt concentration of at least 0.5M and up to about 4.0M.

9. The method of claim 1, wherein the first solid phase and the second solid phase of the mixed-bed solid phase provided in step (a) are anion-exchange solid phases, wherein the first solid phase and the second solid phase each have a different pKa which differ from one another by at least 0.5 pKa units.

10. The method of claim 1, wherein the target nucleic acid is selected from the group consisting of plasmid DNA, genomic DNA, total RNA, and nucleic acids generated by enzymatic amplification.

11. The method of claim 1, wherein the mixture combined with the mixed-bed solid phase in step (d) is a mixture comprising the target nucleic acid and agarose.

12. The method of claim 1, wherein the solution of isolated target nucleic acid is eluted from the mixed-bed solid phase in step (g) only after each of steps (b), (d), (e), and (f) are performed at least once.

13. The method of claim 1, wherein the at least one contaminant is an endotoxin, and wherein at least 90% of the endotoxin present in the mixture is not present in the solution eluted from the mixed-bed phase in step (g).

14. A method of isolating plasmid DNA from a mixture comprising the plasmid DNA and at least one contaminant, the method comprising the steps of:
   a) providing a mixed-bed solid phase comprising a first silica magnetic particle and a second silica magnetic particle, wherein:
      the first magnetic silica particle has a capacity to bind to the plasmid DNA in the presence of a first solution and to release the target nucleic acid in the presence of a second solution, the second silica magnetic particle has a capacity to bind to the plasmid DNA in the presence of the second solution and to release the plasmid DNA in the presence of the first solution, and the first magnetic silica particle and the second magnetic silica particle each have a capacity to release the plasmid DNA bound thereto in the presence of an elution buffer;

b) combining the mixture with the mixed-bed solid phase in the presence of the first solution and permitting the plasmid DNA to bind to the first solid phase;

c) separating the mixed-bed solid phase from the first solution;

d) combining the mixed-bed solid phase with the second solution and permitting the plasmid DNA to release from the first solid phase and bind to the second solid phase;

e) separating the mixed-bed solid phase from the second solution; and f) combining the mixed-bed solid phase with the elution buffer and permitting the plasmid DNA to release from the mixed-bed solid phase into the elution buffer.

15. The method of claim 14, wherein the mixed-bed solid phase provided in step (a) is equilibrated with an equilibration buffer which is substantially free of chaotropic agents prior to combining the equilibrated mixed-bed solid phase with the mixture in step (b).

16. The method of claim 14, wherein magnetic force is used to retain mixed-bed solid phase in a container during at least one removing step selected from steps (d) and (f).

17. The method of claim 14, wherein the first silica magnetic particle comprises at least one anion exchange group covalently attached thereto, and the second silica magnetic particle comprises a siliceous oxide coating.

18. The method of claim 17, wherein the first solution has a pH of at least about 4 and up to about 9 and a salt concentration of at least about 100 mM and up to about 3M; and wherein the second solution has a pH of at least about 4 and up to about 9 and a salt concentration of at least 0.5M and up to about 4.0M.

19. The method of claim 14, wherein the second silica magnetic particle comprises at least one anion exchange group covalently attached thereto, and the first silica magnetic particle comprises a siliceous oxide coating.

20. The method of claim 19, wherein the second solution has a pH of at least about 4 and up to about 9 and a salt concentration of at least about 100 mM and up to about 3M; and wherein the first solution has a pH of at least about 4 and up to about 9 and a salt concentration of at least 0.5M and up to about 4.0M.

21. The method of claim 14, wherein the mixed-bed solid phase is not combined with the elution buffer in step (f) until after each of steps (b), (d), (e), and (f) are performed at least twice.

22. The method of claim 14, wherein the at least one contaminant is an endotoxin, and wherein at least 90% of the endotoxin is not present in the solution eluted from the mixed-bed phase in step (g).

23. A method of isolating genomic DNA from a mixture comprising the genomic DNA and at least one contaminant, the method comprising the steps of:

a) providing a mixed-bed solid phase comprising a first silica magnetic particle and a second silica magnetic particle, wherein:

the first magnetic silica particle has a capacity to bind to the genomic DNA in the presence of a first solution and to release the target nucleic acid in the presence of a second solution, the second silica magnetic particle has a capacity to bind to the genomic DNA in the presence of the second solution and to release the genomic DNA in the presence of the first solution, and the first magnetic silica particle and the second magnetic silica particle each have a capacity to release the genomic DNA bound thereto in the presence of an elution buffer;

b) combining the mixture with the mixed-bed solid phase in the presence of the first solution and permitting the genomic DNA to bind to the first solid phase;

c) separating the mixed-bed solid phase from the first solution;

d) combining the mixed-bed solid phase with the second solution and permitting the genomic DNA to release from the first solid phase and bind to the second solid phase;

e) separating the mixed-bed solid phase from the second solution; and f) combining the mixed-bed solid phase with the elution buffer and permitting the genomic DNA to release from the mixed-bed solid phase into the elution buffer.

24. The method of claim 23, wherein the mixed-bed solid phase provided in step (a) is equilibrated with an equilibration buffer which is substantially free of chaotropic agents prior to combining the equilibrated mixed-bed solid phase with the mixture in step (b).

25. The method of claim 23, wherein magnetic force is used to retain mixed-bed solid phase in a container during at least one removing step selected from steps (d) and (f).

26. The method of claim 23, wherein the first silica magnetic particle comprises at least one anion exchange group covalently attached thereto, and the second silica magnetic particle comprises a siliceous oxide coating.

27. The method of claim 26, wherein the first solution has a pH of at least about 4 and up to about 9 and a salt concentration of at least about 100 mM and up to about 3M; and wherein the second solution has a pH of at least about 4 and up to about 9 and a salt concentration of at least 0.5M and up to about 4.0M.

28. The method of claim 23, wherein the second silica magnetic particle comprises at least one anion exchange group covalently attached thereto, and the first silica magnetic particle comprises a siliceous oxide coating.

29. The method of claim 23, wherein the second solution has a pH of at least about 4 and up to about 9 and a salt concentration of at least about 100 mM and up to about 3M; and wherein the first solution has a pH of at least about 4 and up to about 9 and a salt concentration of at least 0.5M and up to about 4.0M.

30. The method of claim 23, wherein the mixed-bed solid phase is not combined with the elution buffer in step (f) until after each of steps (b), (d), (e), and (f) are performed at least twice.

31. A method of isolating nucleic acids generated by enzymatic amplification from a mixture comprising the nucleic acids and at least one contaminant, the method comprising the steps of:

a) providing a mixed-bed solid phase comprising a first silica magnetic particle and a second silica magnetic particle, wherein:

the first magnetic silica particle has a capacity to bind to the nucleic acids in the presence of a first solution and to release the target nucleic acid in the presence of a second solution, the second silica magnetic particle has a capacity to bind to the nucleic acids in the presence of the second solution and to release the nucleic acids in the presence of the first solution, and the first magnetic silica particle and the second magnetic silica particle each have a capacity to release the nucleic acids bound thereto in the presence of an elution buffer;

b) combining the mixture with the mixed-bed solid phase in the presence of the first solution and permitting the nucleic acids to bind to the first solid phase;

c) separating the mixed-bed solid phase from the first solution;

d) combining the mixed-bed solid phase with the second solution and permitting the nucleic acids to release from the first solid phase and bind to the second solid phase;

e) separating the mixed-bed solid phase from the second solution; and f) combining the mixed-bed solid phase with the elution buffer and permitting the nucleic acids to release from the mixed-bed solid phase into the elution buffer.

32. The method of claim 31, wherein magnetic force is used to retain mixed-bed solid phase in a container during at least one removing step selected from steps (d) and (f).

33. The method of claim 31, wherein the first silica magnetic particle comprises at least one anion exchange group covalently attached thereto, and the second silica magnetic particle comprises a siliceous oxide coating.

34. A method of isolating a target RNA from a mixture comprising the target RNA and DNA, the method comprising the steps of:

a) providing a mixed-bed solid phase comprising a first silica magnetic particle and a second silica magnetic particle, wherein:

the first magnetic silica particle has a capacity to bind to the target RNA in the presence of a first solution and to release the target RNA in the presence of a second solution, the second silica magnetic particle has a capacity to bind to the target RNA in the presence of the second solution and to release the target RNA in the presence of the first solution, and the first magnetic silica particle and the second magnetic silica particle each have a capacity to release the target RNA bound thereto in the presence of an elution buffer;

b) combining the mixture with the mixed-bed solid phase in the presence of the first solution and permitting the target RNA to bind to the first solid phase;

c) separating the mixed-bed solid phase from the first solution;

d) combining the mixed-bed solid phase with the second solution and permitting the target RNA to release from the first solid phase and bind to the second solid phase;

e) separating the mixed-bed solid phase from the second solution; and f) combining the mixed-bed solid phase with the elution buffer and permitting the target RNA to release from the mixed-bed solid phase into the elution buffer.

35. The method of claim 34, wherein magnetic force is used to retain mixed-bed solid phase in a container during at least one removing step selected from steps (d) and (f).

36. The method of claim 34, wherein the first silica magnetic particle comprises at least one anion exchange group covalently attached thereto, and the second silica magnetic particle comprises a siliceous oxide coating.

37. The method of claim 34, wherein the first solution has a pH of at least about 4 and up to about 9 and a salt concentration of at least about 100 mM and up to about 3M; and wherein the second solution has a pH of at least about 4 and up to about 9 and a salt concentration of at least 0.5M and up to about 4.0M.

38. The method of claim 34, wherein the second silica magnetic particle comprises at least one anion exchange group covalently attached thereto, and the first silica magnetic particle comprises a siliceous oxide coating.

39. The method of claim 34, wherein the second solution has a pH of at least about 4 and up to about 9 and a salt concentration of at least about 100 mM and up to about 3M; and wherein the first solution has a pH of at least about 4 and up to about 9 and a salt concentration of at least 0.5M and up to about 4.0M.

* * * * *